(12) United States Patent
Schmeing et al.

(10) Patent No.: US 12,655,401 B2
(45) Date of Patent: Jun. 16, 2026

(54) PROTEIN CONSTRUCTS OF MOLONEY MURINE LEUKEMIA VIRUS REVERSE TRANSCRIPTASE (MMLV-RT)

(71) Applicant: THE ROYAL INSTITUTION FOR THE ADVANCEMENT OF LEARNING/MCGILL UNIVERSITY, Montreal (CA)

(72) Inventors: Thomas Martin Thorne Schmeing, Montréal (CA); Michael John Tarry, Saint Laurent (CA)

(73) Assignee: INTEGREON GLOBAL, INC., Short Hills, NJ (US)

( * ) Notice: Subject to any disclaimer, the term of this patent is extended or adjusted under 35 U.S.C. 154(b) by 707 days.

(21) Appl. No.: 18/012,666

(22) PCT Filed: Jul. 7, 2021

(86) PCT No.: PCT/IB2021/056092
§ 371 (c)(1),
(2) Date: Dec. 23, 2022

(87) PCT Pub. No.: WO2022/009116
PCT Pub. Date: Jan. 13, 2022

(65) Prior Publication Data
US 2023/0348868 A1 Nov. 2, 2023

Related U.S. Application Data

(60) Provisional application No. 63/050,198, filed on Jul. 10, 2020.

(51) Int. Cl.
| | |
|---|---|
| *C12N 9/12* | (2006.01) |
| *C12N 15/70* | (2006.01) |
| *C12Q 1/48* | (2006.01) |

(52) U.S. Cl.
CPC ........... *C12N 9/1276* (2013.01); *C12N 15/70* (2013.01); *C12Q 1/48* (2013.01); *C12Y 207/07049* (2013.01)

(58) Field of Classification Search
CPC ...... C12N 9/1276; C12N 15/70; C12N 15/62; C12Q 1/48; C12Y 207/07049; C07K 2319/00; C07K 2319/20; C07K 2319/21; C07K 2319/50; C12R 2001/19; C12P 21/02
See application file for complete search history.

(56) References Cited

FOREIGN PATENT DOCUMENTS

WO     WO198606741 A1 * 11/1986

OTHER PUBLICATIONS

Whisstock et al. Quaterly Reviews of Biophysics, 2003, "Prediction of protein function from protein sequence and structure", 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Crawford S and Goff SP. A deletion mutation in the 5' part of the pol gene of Moloney Murine a Leukemia Virus blocks proteolytic processing of the gag and pol polyproteins. Mar. 1985, J of Virology vol. 53(3), pp. 899-907, ISSN: 1098-5514.

International Search Report.

* cited by examiner

*Primary Examiner* — Iqbal H Chowdhury
(74) *Attorney, Agent, or Firm* — Eric P. Mirabel

(57) ABSTRACT

Described are protein constructs of Moloney murine leukemia virus reverse transcriptase (MMLV-RT). In one embodiment the protein construct comprises a Moloney murine leukemia virus reverse transcriptase (MMLV) mature protein sequence; and an expression enhancement sequence at the N-terminus of said MMLV mature protein sequence. The expression enhancement sequence is devised for providing heterologous expression of the protein construct in bacterial cells in absence of chaperone co-expression and/or to provide high-level of expression of the MMLV. In another embodiment the protein construct further comprises a tag/ linker combo at the N-terminus of the expression enhancement sequence for assisting in purification of the protein construct. Also described are isolated nucleic acid molecules, vectors and methods for expressing the protein construct in cells. Advantageously these allow large-scale expression of MMLV-RT from cultures of *E. coli* cells and simplify protocols for purification of MMLV-RT at high purity.

2 Claims, 7 Drawing Sheets

Specification includes a Sequence Listing.

MGHHHHHHHHHPDLGTGSENLYFQ*GQPLQVLT*NIEDEHRLHETSKEPDVSLGSTWLSDFPQAWAETGGM
GLAVRQAPLIIPLKATSTPVSIKQYPMSQKARLGIKPHIQRLLDQGILVPCQSPWNTPLLPVKKPGTND
YRPVQDLRBVNKRVEDIHPTVPNPYNLLSGLPPSHQWYTVLDLKDAFFCLRLHPTSQPLFAFEWRDPEM
GISGQLTWTRLPQGFKNSPTLFDEALHRDLADFRIQHPDLILLQYVDDLLLAATSELDCQQGTPALLQT
LGNLGYRASAKKAQICQKQVKYLGYLLKEGQRWLTEARKETVMGQPTPKTPRQLRRFLGTAGFCRLFIP
GFAEMAAPLYPLTKTGTLFNWGPDQQKAYQEIKQALLTAPALGLPDLTKPFELFVDEKQGYAKGVLTQK
LGPWRRPVAYLSKKLDPVAAGWPPCLRMVAAIAVLTKDAGKLTMGQPLVIGAPHAVEALVKQPPDRWLS
KARMTHYQALLLDTDRVQFGFVVALNPATLLPLPEEGLQHNCLDILAEAHGTRPDLTDQPLPDADHTWY
TNGSSLLQEGQRKAGAAVTTETEVIWAKALPAGTSAQRAELIALTQALKMAEGKKLNVYTDSRYAFATA
HIHGEIYRRRGLLTSEGKEIKNKDEILALLKALFLPKRLSIIHCPGHQKGHSAEARGNRMADQAARKAA
ITET        SEQ ID NO:2

FIGURE 1

MGHHHHHHHHHPDLGTGSENLYFQ*GQPLQVLT*NIEDEHRLHETSKEPDVSLGSTWLSDFPQAWAETGGM
GLAVRQAPLIIPLKATSTPVSIKQYPMSQKARLGIKPHIQRLLDQGILVPCQSPWNTPLLPVKKPGTND
YRPVQDLRBVNKRVEDIHPTVPNPYNLLSGLPPSHQWYTVLDLKDAFFCLRLHPTSQPLFAFEWRDPEM
GISGQLTWTRLPQGFKNSPTLFDEALHRDLADFRIQHPDLILLQYVDDLLLAATSELDCQQGTPALLQT
LGNLGYRASAKKAQICQKQVKYLGYLLKEGQRWLTEARKETVMGQPTPKTPRQLRRFLGTAGFCRLFIP
GFAEMAAPLYPLTKTGTLFNWGPDQQKAYQEIKQALLTAPALGLPDLTKPFELFVDEKQGYAKGVLTQK
LGPWRRPVAYLSKKLDPVAAGWPPCLRMVAAIAVLTKDAGKLTMGQPLVIGAPHAVEALVKQPPDRWLS
KARMTHYQALLLDTDRVQFGFVVALNPATLLPLPEEGLQHNCLDILAEAHGTRPDLTDQPLPDADHTWY
TNGSSLLQEGQRKAGAAVTTETEVIWAKALPAGTSAQRAELIALTQALKMAEGKKLNVYTDSRYAFATA
HIHGEIYRRRGLLTSEGKEIKNKDEILALLKALFLPKRLSIIHCPGHQKGHSAEARGNRMADQAARKAA
ITETEDTSTLLI        SEQ ID NO:4

FIGURE 2

A
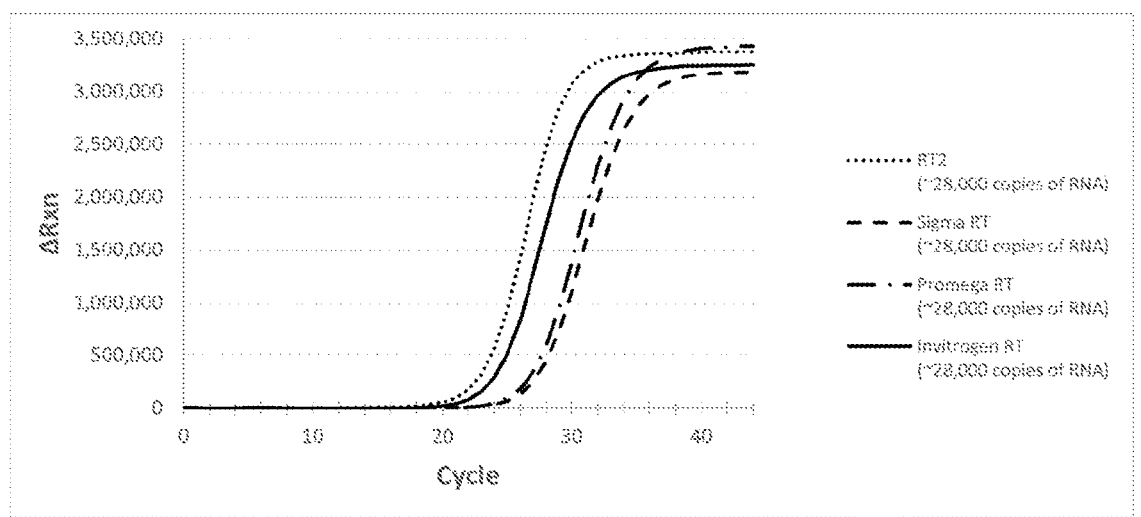
B
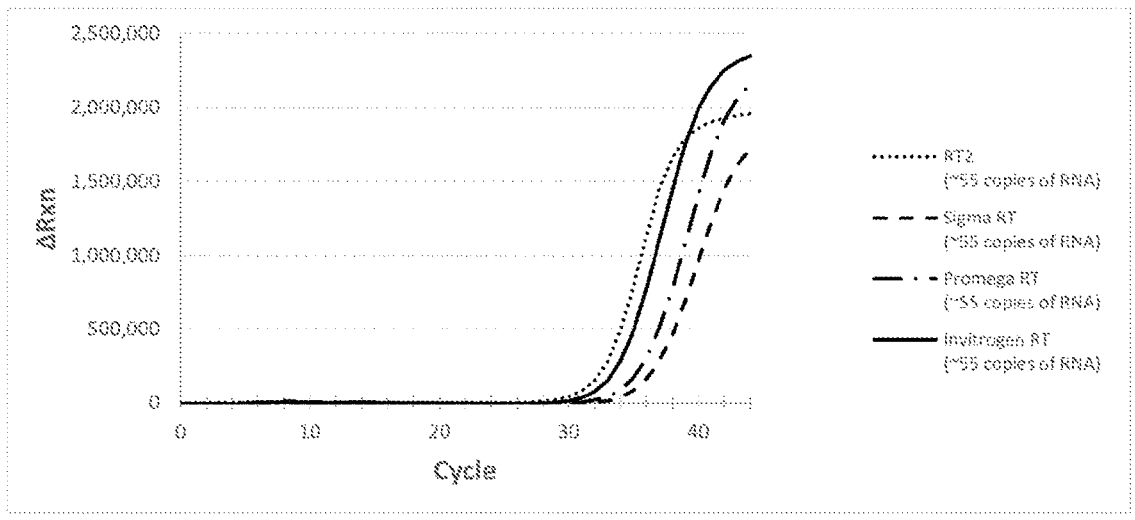
FIGURE 9

PROTEIN CONSTRUCTS OF MOLONEY MURINE LEUKEMIA VIRUS REVERSE TRANSCRIPTASE (MMLV-RT)

CROSS REFERENCE TO RELATED APPLICATION

This application claims priority to U.S. 63/050,19 filed on Jul. 10, 2020, the content of which is incorporated herein by reference in its entirety.

FIELD OF THE INVENTION

The invention relates to the field of protein expression and more particularly to a protein construct of moloney murine leukemia virus reverse transcriptase (MMLV-RT).

BACKGROUND OF THE INVENTION

Ribonucleic acid (RNA) is an important and versatile polymeric biological molecule. It consists of a chain of nucleotide bases, linked by phosphodiester linkages. The sequence of nucleotide bases and the length of the polymer determine the properties and activities. Depending on the sequence, context and identity of the particular RNA molecule, it can function in nature as the messenger intermediate in converting genetic information into protein sequence; it can function as a structural or functional component of a biological complex, it can function as an enzyme or catalyst, and it can function as the storage medium for genetic information. However, RNA is less stable than deoxyribonucleic acid (DNA), and it is less convenient to amplify the numbers of copies of a particular RNA molecule than it is to do so for a DNA molecule of analogous sequence. It is therefore advantageous to produce molecules of DNA which have the analogous sequences to those found in a molecule of interest of RNA. This is a process known as reverse transcription.

The family of enzymes which perform reverse transcription are called reverse transcriptases (RTs). Many wild type and mutated variants of RTs have been commercialized for research and diagnostic purposes, including variants of the RT found in Moloney murine leukemia virus (MMLV). Of particular interest is the use of RTs in clinical laboratory diagnostic tests for RNA viruses, which have RNA as their genetic material, including SARS-CoV-2, the causative virus of the COVID19 pandemic.

Wide scale testing for the virus requires large amounts of RTs, and thus constructs of RTs which are advantageous for production at large scale, possess high specific activity, and function well in SARS-CoV-2 diagnostic tests are desired.

Reverse transcriptases that have been mutated or modified to increase thermostability, decrease terminal deoxynucleotidyl transferase activity, and/or increase fidelity have been described for instance in U.S. Pat. Nos. 7,078,208 and 9,783,791 and by Arezi & Hogrefe (2009, Nucleic Acids Research, 37(2): 473-481). Nevertheless, production of recombinant RTs remains an issue. Chen Y. et al., *Biotechnol Lett* (2009) 31:1051-1057 describe a method for the production of reverse transcriptase from Moloney murine leukemia virus (MMLV-RT) in Escherichia colt but levels of expression of the recombinant RT are still far from being optimal and co-expression of chaperones are required for the expression of the protein construct in bacterial cells.

Accordingly, there is a need for production methods and reverse transcriptase protein constructs providing high-level of expression of heterologous RTs.

There is particularly a need for production methods and Moloney murine leukemia virus reverse transcriptase (MMLV-RT) constructs that can yield to production of at least 50 mg of protein per 1 L of media bacterial cells expressing the MMLV-RT grown in flasks or grown in a fermenter not operated in fed-batch mode.

There is particularly a need for production methods and MMLV-RT constructs wherein co-expression of chaperones is not required for the expression of the protein construct in bacterial cells. A related need exists in isolated nucleic acid molecules encoding such constructs and suitable DNA expression vectors for producing greater amounts of MMLV-RT.

There is also a need kits for performing a reverse transcription reaction and/or for detecting RNA obtained from a subject, for instance for diagnosing a SARS-CoV-2 infection in a subject.

The present invention addresses these needs and other needs as it will be apparent from the review of the disclosure and description of the features of the invention hereinafter.

BRIEF SUMMARY OF THE INVENTION

According to one aspect, the invention relates to a protein construct of Moloney murine leukemia virus reverse transcriptase (MMLV-RT), comprising:

a Moloney murine leukemia virus reverse transcriptase (MMLV) mature protein sequence; and an expression enhancement sequence at the N-terminus of said MMLV mature protein sequence;

wherein said expression enhancement sequence provides for at least one of:

(i) heterologous expression of said protein construct in bacterial cells in absence of chaperone co-expression; and (ii) yield to production of at least 50 mg, or at least 100 mg, or at least 150 mg, or at least 200 mg of said protein construct from 1 L of media when bacterial cells transformed with a vector encoding said protein construct are grown in flasks or grown in a fermenter not operated in fed-batch mode.

According to another aspect, the invention relates to a protein construct of Moloney murine leukemia virus reverse transcriptase (MMLV-RT), comprising:

(a) a Moloney murine leukemia virus reverse transcriptase (MMLV) mature protein sequence;

(b) an expression enhancement sequence at the N-terminus of said MMLV mature protein sequence; and (c) a tag/linker combo at the N-terminus of the expression enhancement sequence for assisting in purification of said protein construct.

According to another aspect, the invention relates an isolated nucleic acid molecule encoding an isolated protein construct as defined herein.

According to another aspect, the invention relates to a DNA expression vector for producing a Moloney murine leukemia virus reverse transcriptase (MMLV-RT) protein, said DNA vector comprising an isolated nucleic acid molecule as defined herein.

According to another aspect, the invention relates to a method of producing Moloney murine leukemia virus reverse transcriptase (MMLV-RT) protein, comprising the steps of:

(a) culturing in a culture medium a host cell harboring a DNA expression vector as defined herein;

(b) expressing the MMLV-RT protein encoded by the DNA expression vector; and (c) isolating the MMLV-RT protein from the host cell.

According to another aspect, the invention relates to a reverse transcription reaction kit for performing a reverse transcription reaction, comprising a protein construct as defined herein and one or more of a ready-to-use reagent mixture for reverse transcription polymerase chain reaction (RT-PCR), sample collecting tube(s), reaction tube(s), microplate(s), buffer for the homogenization of sample(s), incubation buffer(s), assay buffer(s), fluorescent and/or luminogenic detection materials, desalting column(s), purified control purified RNA or cDNA and a user manual or instructions.

According to another aspect, the invention relates to a diagnostic kit comprising a protein construct as defined herein, and reagent for detecting RNA obtained from a subject.

Additional aspects, advantages and features of the present invention will become more apparent upon reading of the following non-restrictive description of preferred embodiments which are exemplary and should not be interpreted as limiting the scope of the invention.

BRIEF DESCRIPTION OF THE FIGURES

In order for the invention to be readily understood, embodiments of the invention are illustrated by way of example in the accompanying figures.

FIG. 1 shows the amino acid sequence of a Moloney murine leukemia virus reverse transcriptase (MMLV-RT) protein construct, referred to as "RT2", in accordance with one embodiment of the present invention. This amino acid sequence is also depicted in SEQ ID NO: 2. The portion of the sequence shaded in grey (i.e. starting with "LN" and ending with "ET") corresponds to a MMLV-RT mature protein sequence with a C-terminal truncation of 8 amino acids. Amino acids in bold (K,R,F,G,K) represent mutations in wild-type MMLV-RT, and the white amino acid in a black background (N) corresponds to an RNAse H mutation. Amino acids in double underlined correspond to one example of an expression enhancement sequence as defined herein. Amino acids in bold italics are AA derived from MMLV pro-protein sequence Pr180.

FIG. 2 shows the amino acid sequence of a Moloney murine leukemia virus reverse transcriptase (MMLV-RT) protein construct in accordance with another embodiment of the present. This amino acid sequence is also depicted in SEQ ID NO: 4. This construct is substantially identical to the construct of FIG. 1, but for an additional eight underlined (8) AA at the C-terminus of the mature MMLV-RT mature protein.

FIG. 9A is a line graph showing the performance of RT2 vs. commercially purchased RT enzymes in RT-qPCR based on fluorescent probes using high template concentrations. Different commercial RT at 10 U/ul (Sigma RT: M-MLV Reverse Transcriptase, M1427-5KU; Promega RT: M-MLV Reverse Transcriptase, M170A; Invitrogen RT: ThermoFisher Superscript™ II 18064022), were compared to 10 U/ul RT2 (estimated specific activity of 1,000,000 U/mg). RT-qPCR reactions used Corman™ E gene primers at 600 nM and Corman E gene probe at 200 nM, to amplify and detect template from ATCC diluted by 1:100 (resulting in ~28,000 template RNA molecules per reaction).

FIG. 9B is a line graph showing the performance of RT2 vs. commercially purchased RT enzymes in RT-qPCR based on fluorescent probes using low template concentrations. Different purchased commercial RT at 10 U/ul (Sigma RT: M-MLV Reverse Transcriptase, M1427-5KU; Promega RT: M-MLV Reverse Transcriptase, M170A; Invitrogen RT: ThermoFisher Superscript™ II 18064022), were compared to 10 U/ul RT2 (estimated specific activity of 1,000,000 U/mg). RT-qPCR reactions used Corman™ E gene primers at 600 nM and Corman E gene probe at 200 nM, to amplify and detect template from ATCC diluted by 1:50,000 (resulting in -55 template RNA molecules per reaction).

Figure 3:
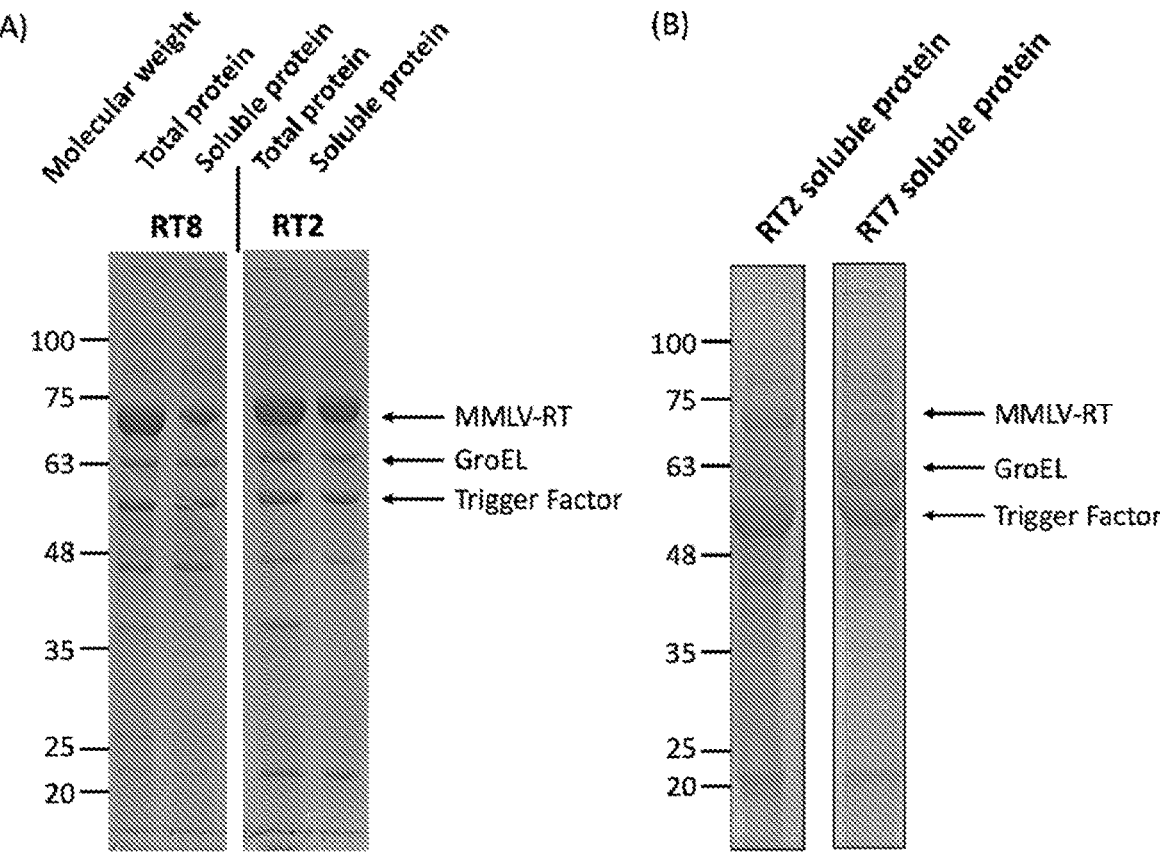
FIG. 3 is a panel with pictures showing the expression levels of soluble RT2, in comparison in (A) with RT construct RT8, and in (B) with construct RT7 in the presence of chaperones.

Further details of the invention and its advantages will be apparent from the detailed description included below.

DETAILED DESCRIPTION OF EMBODIMENTS

In the following description of the embodiments, references to the accompanying figures are illustrations of an example by which the invention may be practiced. It will be understood that other embodiments may be made without departing from the scope of the invention disclosed. Unless defined otherwise, all technical and scientific terms used herein have the same meaning as commonly understood by one of ordinary skill in the art to which the invention belongs.

General Overview

The invention pertains to means of increasing protein expression of a reverse transcriptase enzyme, and more particularly Moloney murine leukemia virus reverse transcriptase (MMLV-RT).

The present inventors have devised protein constructs of MMLV-RT and production methods providing high-level of expression of the heterologous RT in cells, including bacterial cells. Another advantage of the present protein constructs is associated with the fact heterologous expression of these protein constructs in bacterial cells is achieved in absence of chaperone co-expression, thereby not requiring licensing of third-party chaperone expression plasmids, not requiring separation of co-expressed chaperones from RT during purification steps and not producing quasi-stable (RT) protein which is partially misfolded (a common problem with chaperone co-expression). The protein constructs may also comprise additional useful features such as affinity tag to facilitate purification.

Another advantage of the present invention is that it allows for high purity purification of recombinant RTs, particularly Moloney murine leukemia virus reverse transcriptases (MMLV-RTs).

Protein Constructs

One aspect of the invention concerns engineered protein constructs for recombinant expression of reverse transcriptase (RT), the key enzyme required for conversion of RNA to DNA. The engineered protein constructs are advantageously expressed at high-level levels in bacterial cells and do not require co-expression of chaperones in bacterial cells.

According to one particular aspect, the protein construct is a protein construct of Moloney murine leukemia virus reverse transcriptase (MMLV-RT), comprising: (a) a Moloney murine leukemia virus reverse transcriptase (MMLV) mature protein sequence; and (b) an expression enhancement sequence at the N-terminus of the MMLV mature protein sequence.

As used herein, the term "expression enhancement sequence" or "EES" refers to an amino acid sequence that is configured for increasing heterologous soluble expression of stable MMLV-RT. According to the present invention, the expression enhancement sequence provides for at least one of: (i) heterologous expression of MMLV-RT protein construct(s) in bacterial cells in absence of chaperone co-expression; and (ii) yield to production of at least 50 mg, or at least 100 mg, or at least 150 mg, or at least 200 mg of the protein construct(s) per 1 L of media when bacterial cells transformed with a vector encoding said protein construct are grown in flasks or grown in a fermenter not operated in fed-batch mode. In preferred embodiments, for achieving said increased expression, the EES is at the N-terminus of the MMLV mature protein sequence.

In one embodiment, the expression enhancement sequence comprises at least one amino acid selected from the sequence as set forth in SEQ ID NO: 5 or SEQ ID NO: 7 and/or as defined in Table 1 below:

TABLE 1

Examples of an expression enhancement sequences (1/2)

| A | -21 | -20 | -19 | -18 | -17 | -16 | -15 | -14 | -13 | -12 | ... ... ... | -11 |
|---|-----|-----|-----|-----|-----|-----|-----|-----|-----|-----|-------------|-----|
| B | $Xaa_1$ | $Xaa_2$ | $Xaa_3$ | $Xaa_4$ | $Xaa_5$ | $Xaa_6$ | $Xaa_7$ | $Xaa_8$ | $Xaa_9$ | $Xaa_{10}$ | ... ... ... | $Xaa_{11}$ |
| C | P | D | L | G | T | G | S | E | N | L | ... ... ... | Y |

| A | -10 | -9 | -8 | -7 | -6 | -5 | -4 | -3 | -2 | -1 |
|---|-----|----|----|----|----|----|----|----|----|----|
| B | $Xaa_{12}$ | $Xaa_{13}$ | $Xaa_{14}$ | $Xaa_{15}$ | $Xaa_{16}$ | $Xaa_{17}$ | $Xaa_{18}$ | $Xaa_{19}$ | $Xaa_{20}$ | $Xaa_{21}$ |
| C | F | Q | G | Q | P | L | Q | V | L | T |

Row A: Corresponds to the position of the amino acid (AA) relative to the N-terminus of the MMLV mature protein sequence Row B: Consists of SEQ ID NO: 7, wherein:

Each of $Xaa_1$ and $Xaa_{16}$ can be represented by any amino acid of P, G, S, A or T Each of $Xaa_2$, $Xaa_8$, $Xaa_9$, $Xaa_{13}$, $Xaa_{15}$, and $Xaa_{18}$ can be represented by any amino acid of D, E, N or Q Each of $Xaa_3$, $Xaa_4$, $Xaa_6$, $Xaa_{10}$, $Xaa_{17}$, $Xaa_{19}$ and $Xaa_{20}$ can be represented by any amino acid of G, A, V, L or I Each of $Xaa_5$, $Xaa_7$, and $Xaa_{21}$ can be represented by any amino acid of S, C, T or M Each of $Xaa_{11}$, and $Xaa_{12}$ can be represented by any amino acid of F, Y or W $Xaa_{14}$ can be represented by any amino acid of S, G, A, V, L or I Row C: Corresponds to amino acids as set forth in SEQ ID NO: 5.

In another embodiment, the expression enhancement sequence comprises at least one amino acid selected from the sequence as set forth in SEQ ID NO: 6 or SEQ ID NO: 8 and defined in Table 2 below:

TABLE 2

Examples of an expression enhancement sequences (2/2)

| A | −21 | −20 | −19 | −18 | −17 | −16 | −15 | −14 | −13 | −12 | . . . . . . | −11 |
|---|---|---|---|---|---|---|---|---|---|---|---|---|
| B | Xaa$_1$ | Xaa$_2$ | Xaa$_3$ | Xaa$_4$ | Xaa$_5$ | Xaa$_6$ | Xaa$_7$ | Xaa$_8$ | Xaa$_9$ | Xaa$_{10}$ | . . . . . . | Xaa$_{11}$ |
| C | H | F | E | G | S | G | A | Q | V | M | . . . . . . | G |

| A | −10 | −9 | | −8 | −7 | | −6 | −5 | | −4 | −3 | | −2 | −1 |
|---|---|---|---|---|---|---|---|---|---|---|---|---|---|---|
| B | Xaa$_{12}$ | Xaa$_{13}$ | | Xaa$_{14}$ | Xaa$_{15}$ | | Xaa$_{16}$ | Xaa$_{17}$ | | Xaa$_{18}$ | Xaa$_{19}$ | | Xaa$_{20}$ | Xaa$_{21}$ |
| C | P | M | | G | Q | | P | L | | Q | V | | L | T |

Row A: Corresponds to the position of the amino acid (AA) relative to the N-terminus of the MMLV mature protein sequence Row B: Consists of SEQ ID NO: 8, wherein:

Xaa$_1$ can be represented by any amino acid of H, K or R

Xaa$_2$ can be represented by any amino acid of F, Y or W

Each of Xaa$_3$, Xaa$_8$, Xaa$_{15}$, and Xaa$_{18}$ can be represented by any amino acid of D, E, N or Q Each of Xaa$_4$, Xaa$_6$, Xaa$_7$, Xaa$_9$, Xaa$_{11}$, Xaa$_{14}$, Xaa$_{17}$, Xaa$_{19}$ and Xaa$_{20}$ can be represented by any amino acid of G, A, V, L or I Each of Xaa$_5$, Xaa$_{10}$, Xaa$_{13}$ and Xaa$_{21}$ can be represented by any amino acid of S, C, T or M Each of Xaa$_{12}$, and Xaa$_{16}$ can be represented by any amino acid of P, G, S, A or T Row C: Corresponds to amino acids as set forth in SEQ ID NO: 6.

In embodiments, the expression enhancement sequence comprises at least 2, or at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or at least 21 consecutive amino acids from the C-terminus of SEQ ID NO: 5, or from the C-terminus of SEQ ID NO: 6, or from the C-terminus of SEQ ID NO: 6, or from the C-terminus of SEQ ID NO: 8.

In embodiments, the expression enhancement sequence comprises at least 2, or at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or at least 21 consecutive amino acids from the N-terminus of SEQ ID NO: 5, or from the N-terminus SEQ ID NO: 6, or from the N-terminus SEQ ID NO: 6, or from the N-terminus SEQ ID NO: 8.

In embodiments, the expression enhancement sequence is other than MGQPLQVLT (SEQ ID NO: 9). In embodiments, the expression enhancement sequence comprises at least 9 amino acids at the N-terminus of said MMLV mature protein sequence, and the amino acid at position minus 9 is other than a methionine. In embodiments, the expression enhancement sequence comprises at least 8 amino acids at the N-terminus of the MMLV mature protein sequence. In embodiments, the expression enhancement sequence comprises at least 8 amino acids at the N-terminus of the MMLV mature protein sequence, and the amino acid at position minus 8 is a glycine.

In embodiments, the expression enhancement sequence (EES) is selected from the group consisting of:

```
                              (SEQ ID NO: 10)
T, LT, VLT, QVLT, (SEQ ID NO: 11)
LQVLT, (SEQ ID NO: 12)
PLQVLT,
```

```
                              (SEQ ID NO: 13)
QPLQVLT, (SEQ ID NO: 14)
GQPLQVLT, (SEQ ID NO: 15)
QGQPLQVLT, (SEQ ID NO: 16)
FQGQPLQVLT, (SEQ ID NO: 17)
YFQGQPLQVLT, (SEQ ID NO: 18)
LYFQGQPLQVLT, (SEQ ID NO: 19)
NLYFQGQPLQVLT, (SEQ ID NO: 20)
ENLYFQGQPLQVLT, (SEQ ID NO: 21)
SENLYFQGQPLQVLT, (SEQ ID NO: 22)
GSENLYFQGQPLQVLT, (SEQ ID NO: 23)
TGSENLYFQGQPLQVLT, (SEQ ID NO: 24)
GTGSENLYFQGQPLQVLT, (SEQ ID NO: 25)
LGTGSENLYFQGQPLQVLT, (SEQ ID NO: 26)
DLGTGSENLYFQGQPLQVLT, (SEQ ID NO: 37)
PMGQPLQVLT, (SEQ ID NO: 27)
GPMGQPLQVLT, (SEQ ID NO: 28)
MGPMGQPLQVLT,
```

−continued

-continued

```
                                      (SEQ ID NO: 29)
VMGPMGQPLQVLT, (SEQ ID NO: 30)
QVMGPMGQPLQVLT, (SEQ ID NO: 31)
AQVMGPMGQPLQVLT, (SEQ ID NO: 32)
GAQVMGPMGQPLQVLT, (SEQ ID NO: 33)
SGAQVMGPMGQPLQVLT, (SEQ ID NO: 34)
GSGAQVMGPMGQPLQVLT, (SEQ ID NO: 35)
EGSGAQVMGPMGQPLQVLT,
and (SEQ ID NO: 36)
FEGSGAQVMGPMGQPLQVLT.
```

The protein construct and/or expression enhancement sequence may also comprise additional features. In embodiments, the expression enhancement sequence comprises a protease cleavage sequence (e.g. see hereinafter). In embodiments, the expression enhancement sequence comprises a linker sequence for linking the MMLV mature protein sequence to an affinity tag (e.g. see hereinafter). In embodiments, the protein construct further comprises an affinity tag at the N-terminus of the expression enhancement sequence (e.g. see hereinafter).

According to another particular aspect, the protein construct is a protein construct of Moloney murine leukemia virus reverse transcriptase (MMLV-RT), comprising: (a) a Moloney murine leukemia virus reverse transcriptase (MMLV) mature protein sequence; (b) an expression enhancement sequence at the N-terminus of said MMLV mature protein sequence; and (c) a tag/linker combo at the N-terminus of the expression enhancement sequence for assisting in purification of said protein construct.

The tag/linker combo can be varied in length and in amino acid sequence. In embodiments the tag/linker combo comprises an affinity tag. The affinity tag may be selected from any useful affinity tag including, but not limited to a histidine tag, a glutathione S-Transferase tag, a maltose binding protein affinity tag, thioredoxin His-patch tag, a calmodulin binding peptide tag, an intein-chitin binding domain tag, a streptavidin-binding peptide tag, a flag tag, a SUMO tag, and a Halo tag. In particular embodiments, the affinity tag is histidine tag comprising from 5 to 12 consecutive histidine residues (e.g. a His8 affinity tag (HHHHHHHH, SEQ ID NO: 38).

In embodiments the tag/linker combo comprises a protease cleavage sequence. The protease cleavage sequence may be a Tobacco Etch Virus (TEV) protease cleavage sequence, for instance the amino acid sequence E-X-X-Y-X-Q-(G/S) (SEQ ID NO: 39) where X can be any amino acid. One particular example is ENLYFQG (SEQ ID NO: 40) where the G is both the last residue in the TEV protease cleavage sequence and the first residue in the reverse transcriptase construct. The protease cleavage sequence may also comprise an amino acid sequence selected from VSQTSKLTRAETVFPDV (SEQ ID NO: 41), PLGLWA (SEQ ID NO: 42), RVLAEA (SEQ ID NO: 43), EDVVCCSMSY (SEQ ID NO: 44), GGIEGRGS (SEQ ID NO: 45), TRHRQPRGWE (SEQ ID NO: 46), AGNRVRRSVG (SEQ ID NO: 47), RRRRRRRRR (SEQ ID NO: 48), GFLG (SEQ ID NO: 49), DDDDK (SEQ ID NO: 50), LVPRGS (SEQ ID NO: 51), and LEVLFQGP (SEQ ID NO: 52). In embodiments the protease cleavage sequence comprises an amino acid sequence other than DDDDK (SEQ ID NO: 53) or other than LVPRGS (SEQ ID NO: 54).

In embodiments the tag/linker combo comprises an affinity tag, a protease cleavage sequence and an amino acid linker between the affinity tag and the protease cleavage sequence.

In embodiments the tag/linker combo does not comprises the amino acid sequence SSGLVPRGSH-MASMTGGQQMGRGSDDDDKM (SEQ ID NO: 55) and/or does not comprises a sequence comprising least 4 consecutive amino acids of SEQ ID NO: 55.

The amino acid linker may be selected from serine-glycine linkers, flexible linkers and rigid linkers. Examples of serine-glycine linker include, but are not limited to,(GS)n, (SG)n, (GGS)n, (GGGS)n (SEQ ID NO: 56), (GSS)n, (GSG)n, (SSG)n, and (GGGGS)n (SEQ ID NO: 57), where n is an integer between 1 and 10. Examples of flexible linkers include, but are not limited to, (A)n, (G)n, (S)n, (ASS)n, (DS)n, and (ARTIN)n (SEQ ID NO: 58), where n is an integer between 1 and 10. Examples of rigid linkers include, but are not limited to (EEEK)n (SEQ ID NO: 59), (EAAAK)n (SEQ ID NO: 60), A(EAAAK)nALEA (EAAAK)nA (SEQ ID NO: 61), PAPAP (SEQ ID NO: 62), (PA)n, (P)n, and (AP)n, where n is an integer between 1 and 10. It is conceivable to use many other linkers. Additional examples of suitable linkers may be found in Chen et al. Adv Drug Deliv Rev., 2013, 65(10): 1357-1369; and Waugh D. S., Protein Expr Purif. 2011, 80(2): 283-293. In one embodiment the amino acid linker is a serine-glycine linker comprising PDLGTGS (SEQ ID NO: 63).

In one particular embodiment the tag/linker combo comprises, or consists of, MGHHHHHHHHPDLGTGSEN-LYFQ (SEQ ID NO: 64). In another particular embodiment the tag/linker combo comprises, or consists of, MGHHHHHHHHPDLGTGSENLYFQG (SEQ ID NO: 65). In another particular embodiment the tag/linker combo comprises, or consists of, MGHHHHHHHHPDLGTGSEN-LYFQS (SEQ ID NO: 66).

Any mature reverse transcriptase protein sequence resulting in expression of a biologically active reverse transcriptase may be used in accordance with the principles of the present invention. One particular example of a suitable mature reverse transcriptase protein sequence is mature MMLV reverse transcriptase (see NCBI accession number NP_955591.1). The mature reverse transcriptase protein sequence may also be derived from pro-enzyme Pr180 (see NCBI accession number NP_057933.2). The mature reverse transcriptase protein sequence according to the invention may also comprise mutation(s) eliminating RNAse H activity, mutation(s) increase thermostability, and the like. Examples of possible mutations include, but are not limited to, those described by Arezi & Hogrefe (Nucleic Acids Research, 2009, Vol. 37, No. 2 473-481). These mutations eliminate RNAse H activity (D524N in mature enzyme or D1183N in pro-enzyme) or increase thermostability (E69K, E302R, W313F, L435G and N454K in mature enzyme numbering or E728K, E961 R, W972F, L1094G and N1113K in pro-enzyme).

In embodiments the MMLV mature protein sequence comprises at least 90%, or at least 95%, at least 97%, at least 98%, or at least 99%, or at least 99.5%, or at least 99.9%, sequence identity, with the amino acid sequence as set forth in SEQ ID NO: 67 or as set forth in SEQ ID NO: 68 or as set forth in NCBI accession number NP_955591.1. In embodiments the MMLV mature protein sequence comprises the amino acid sequence as set forth in SEQ ID NO: 67 or SEQ ID NO: 68. or as set forth in NCBI accession number NP_955591.1. In embodiments the MMLV protein sequence consists of the amino acid sequence as set forth in SEQ ID NO: 67 or SEQ ID NO: 68.

In embodiments, the MMLV protein sequence in accordance with the present invention comprises a specific activity of at least 1,000,000 units per milligram, or at least 800,000 units per milligram, or at least 400,000 units per milligram, or at least 100,000 units per milligram, or at least 10,000 units per milligram, wherein one unit of specific activity is defined as the amount of enzyme required to incorporate 1 nmol of dTTP into acid insoluble material in 10 minutes at 37° C. using poly r(A)/oligo (dT) as a substrate.

In embodiments, the protein construct in accordance to the present invention, comprises one or more of the following properties:

a. is expressed in an expression vector, preferably under induction, including but not limited to vector pET24a using IPTG induction and vector pLMAR using rhamnose induction;

b. is expressed in suitable bacterial cells, including but not limited to E. coli BL21 (DE3), E. coli BL21, and E. coli ΔrhaB (B0002);

c. is expressed without requiring chaperone co-expression;

d. is expressed under suitable temperature and media, e.g. about 16° C. to about 26° C. in terrific broth (TB)-kanamycin (50 mg/L);

e. can be purified from culture media without cleavage of the linker (if any);

f. even in embodiments where a tag/linker combo is present, it possesses a reverse transcriptase activity which is substantially similar to reverse transcriptase activity of a MMLV not coupled to a tag/linker combo;

g. it can yield to the production of at least 50 mg, or at least 100 mg, or at least 150 mg, or at least 200 mg of protein construct per 1 L of media when bacterial cells transformed with a vector encoding the protein construct are grown in flasks or grown in a fermenter not operated in fed-batch mode;

h. comprises and/or results in production of a mature MMLV protein having a specific activity of at least 1,000,000 units per milligram, or at least 800,000 units per milligram, or at least 400,000 units per milligram, or at least 100,000 units per milligram, or at least 10,000 units per milligram, as defined hereinabove.

Table 3 below summarizes some of the properties associated with particular MMLV-RT protein constructs in accordance with the present invention.

TABLE 3

| Properties of MMLV-RT protein constructs RT1, RT2, RT4, RT7, and RT8 | | | | | |
|---|---|---|---|---|---|
| | Expression level | Chaperones | Tag cleavage | Optimized yield per litre flask | Activity in intercalating dye based RT-qPCR | Activity in probe based RT-qPCR |
| RT1 | high | required | necessary | 21 mg/L | | |
| RT2 | high | not required | not necessary | ≥120 mg/L | excellent | excellent |
| RT4 | high | | necessary | | | |
| RT7 | low | | | | | |
| RT8 | low | | | | lower | lower |

Isolated Nucleic Acid Molecules, Expression Vectors and Production Methods

Another aspect of the invention concerns isolated nucleic acid molecules encoding any of the protein constructs defined herein, as well as any portion thereof (e.g. MMLV mature protein sequences, expression enhancement sequences and/or tag/linker combo). In preferred embodiments, the isolated nucleic acid molecules comprise a sequence which has been optimized for expression in bacteria, e.g. *E. coli*.

In embodiments, the isolated nucleic acid encodes a protein construct as set forth in SEQ ID NO: 2 or SEQ ID NO: 4.

In embodiments, the isolated nucleic acid molecule comprises SEQ ID NO: 1 or SEQ ID NO: 3 or it comprises a sequence having at least 90%, or at least 95%, at least 97%, at least 98%, or at least 99%, or at least 99.5%, or at least 99.9%, sequence identity, with the SEQ ID NO: 1 or SEQ ID NO: 3. Preferably the isolated nucleic acid molecule encodes a biologically active MMLV-RT, more preferably a MMLV-RT having a reverse transcriptase activity corresponding to at least 90%, or at least 95%, at least 97%, at least 98%, or at least 99%, or at least 99.5%, or at least 99.9% or more of the reverse transcriptase activity of SEQ ID NO: 67 or SEQ ID NO: 68.

A related aspect of the invention concerns expression vectors for expressing the protein constructs as defined herein and/or comprising an isolated nucleic acid molecules encoding any of the protein constructs defined herein. The present invention encompassed any suitable expression vectors including, but not limited to, plasmids, viruses, cosmids, bacmids, shuttle vectors, artificial chromosomes, etc. In one particular embodiment, the expression vector is a plasmid. Examples of potentially useful plasmid include, but are not limited to, pET24a, pLMAR, pALTER-Ex1, pALTER-Ex2, pBAD/His, pBAD/Myc-His, pBAD/gIII, pBacP, pBac, pBacPTandem, pBacTandem, pBacPTandem, pBacTandem-Rev, pCal-n, pCal-n-EK, pCal-c, pCal-Kc, pcDNA 2.1, pDUAL, pET-3a-c, pET-9a-d, pET-11a-d, pET-12a-c, pET-14b, pET-15b, pET-16b, pET-17b, pET-19b, pET-20b(+), pET-21a-d(+), pET-22b(+), pET-23a-d(+), pET-24b-d(+), pET-25b(+), pET-26b(+), pET-27b(+), pET-28a-c(+), pET-29a-c(+), pET-30a-c(+), pET-31b(+), pET-32a-c(+), pET-33b(+), pET-34b(+), pET-35b(+), pET-36b(+), pET-37b(+), pET-38b(+), pET-39b(+), pET-40b(+), pET-41a-c(+), pET-42a-c(+), pET-43a-c(+), pETBlue-1, pETBlue-2, pETBlue-3, pGEMEX-1, pGEMEX-2, pGEX-1 IT, pGEX-2T, pGEX-2TK, pGEX-3X, pGEX-4T, pGEX-5X, pGEX-6, P, pHAT10/11/12, pHAT20, pHAT-GF, Puv, pKK223-3, pLEX, pMAL-c2X, pMAL-c2E, pMAL-c2G, pMAL-, p2X, pMAL-,p2E, pMAL-, p2G, p, ProEX HT, p, PROLar.A, p, PROTet.E, pQE-9, pQE-16, pQE-30/31/32, pQE-40, pQE-60, pQE-70, pQE-80/81/82L, pQE-100, pRSET, pSE280, pSE380, pSE420, pThioHis, pTrc99A, pTrcHis, pTrcHis2, pTriEx-1, pTriEx-2, pTrxFus, pBP26, pBP27,pBQ200, pGP380, pGP382, pGP3273, pGM1202.

In accordance with the present invention, expression of the reverse transcriptase may be carried out in any suitable cell including, but not limited to, bacterial cells, fungal cells, insect cells, mammalian cells, etc. In embodiments the cells are *E. coli* bacterial cells such as *E. coli* BL21 (DE3), *E. coli* BL21, and in *E. coli* ΔrhaB (B0002). In embodiments the cells are *E. coli* BL21(DE3)-pLysS, *E. coli* BL21 Star-pLysS, *E. coli* BL21-SI, *E. coli* BL21-Al, *E. coli* Tuner, *E. coli* Tuner pLysS, *E. coli* Origami, *E. coli* Origami B, *E. coli* Origami B pLysS, *E. coli* Rosetta, *E. coli* Rosetta pLysS, *E. coli* Rosetta-gami-pLysS, *E. coli* Rosetta2, *E. coli* Rosetta2 pLysS, *E. coli* BL21 CodonPlus, *E. coli* AD494, *E. coli* BL21trxB, *E. coli* HMS174, *E. coli* NovaBlue(DE3), *E. coli* BLR, *E. coli* C41(DE3), *E. coli* C43(DE3), *E. coli* Lemo21 (DE3), *E. coli* SHuffle T7, *E. coli* ArcticExpress, *E. coli* ArcticExpress (DE3). In embodiments the cells are *Streptomyces lividans, Lactoccocus lactis* and *Bacillus subtilis*.

Another aspect of the invention concerns methods of producing the proteins constructs defined herein, including a MMLV-RT construct. In one embodiment the method comprises the steps of:
- (a) culturing in a culture medium a suitable host cell as defined above (e.g. *E. coli*) harboring the DNA expression vector as defined herein;
- (b) expressing the MMLV-RT protein encoded by the DNA expression vector; and
- (c) isolating the MMLV-RT protein from the host cell.

In one embodiment, step (c) comprises the following sub-steps:
- (ci) harvesting the cells and collecting a pellet of harvested cells;
- (cii) resuspending the pellet in a buffer;
- (ciii) lysing said resuspended pellet;
- (civ) centrifuging the resuspended pellet for generating a supernatant; and
- (cv) passing the supernatant through an affinity column to isolate the MMLV-RT protein.

Any suitable affinity column may be used on accordance with the present invention. In embodiments the protein construct comprises a tag/linker combo having an affinity tag and the affinity column is selected for capturing the affinity tag, and vice-versa. In one particular embodiment the affinity column is a nickel affinity chromatography column.

In embodiments, the buffer is at least one of:
Buffer RT-A: 20 mM HEPES pH 8, 300 mM NaCl, 20 mM imidazole, 0.5% Triton X100™, 10% glycerol, 1 mM DTT;
Buffer RT-B: 20 mM HEPES pH 8, 2 M NaCl, 0.5% Triton X100™, 10% glycerol, 1 mM DTT;
Buffer RT-C: 20 mM HEPES pH 8, 300 mM NaCl, 250 mM imidazole, 0.5 % Triton X100™, 10% glycerol, 1 mM DTT;
Buffer RT-D: 20 mM HEPES pH 8, 10% glycerol, 1 mM DTT; and
Buffer RT-E: 20 mM HEPES pH 8, 500 mM NaCl 10% glycerol, 1 mM DTT.

In embodiments, the method yields to production of at least 50 mg, or at least 100 mg, or at least 150 mg, or at least 200 mg of protein construct per liter of culture medium when grown in flasks or when grown in a fermenter not operated in fed-batch mode.

Kits

Another aspect of the present invention concerns reverse transcription reaction kits for performing a reverse transcription reaction. In one embodiment the kit comprises at least one protein construct as defined herein, and one or more of a ready-to-use reagent mixture for reverse transcription polymerase chain reaction (RT-PCR), sample collecting tube(s), reaction tube(s), microplate(s), buffer for the homogenization of sample(s), incubation buffer(s), assay buffer(s), fluorescent and/or luminogenic detection materials, desalting column(s), purified control purified RNA or cDNA and a user manual or instructions.

According to another related aspect of the present invention concerns a diagnostic kit, comprising at least one protein construct as defined herein and a reagent for detecting RNA obtained from a subject. In embodiments the RNA is viral RNA. According to one particular embodiment the kit is for diagnosing a SARS-CoV-2 infection in a subject.

Those skilled in the art will recognize, or be able to ascertain, using no more than routine experimentation, numerous equivalents to the specific procedures, embodiments, claims, and examples described herein. Such equivalents are considered to be within the scope of this invention, and covered by the claims appended hereto. The invention is further illustrated by the following examples, which should not be construed as further or specifically limiting.

EXAMPLES

Example 1: Production and Purification of a Variant of Moloney Murine Leukemia Virus Reverse Transcriptase (MMLV-RT) from Cultures of *E. coli* Cells Several novel constructs of MMLV-RT were designed. One particular construct is described herein and is referred as "RT2". Construct RT2 resulted in the advantageous combinations of high expression of soluble protein in the absence of co-expressed chaperones, robust biophysical properties, facile expression and highly specific activity. RT2 further comprises a combination of affinity tag, linker, and protease cleavage site sequences which resulted in a surprising advantage over existing reverse transcriptases described previously by Arezi & Hogrefe (2009, Nucleic Acids Research, 37(2): 473-481) and Chen Y. et al., *Biotechnol Lett* (2009) 31:1051-1057.

Several gene constructs were cloned into several expression vectors. This allowed investigation of the potential for soluble expression of various RT variants. One of these gene construct, and the corresponding protein construct encoding thereby, is depicted in SEQ ID NO: 2 (see FIG. 1). This construct corresponds to a variant of Moloney murine leukemia virus reverse transcriptase and is herein referred to as RT2. As shown hereinafter, RT2 is a construct with superior levels of heterologous expression in cultures of *E. coli* cells which do not co-express chaperone proteins, robust biophysical properties which allow facile purification, and highly specific activity.

Additional constructs include those with dedicated expression enhancer tags (RT4, RT7). Table 4 reports detail of constructs used herein.

TABLE 4

Description of constructs that were used

| Name | Description |
| --- | --- |
| RT1 | Construct reported in Chen et al. (supra) |
| *RT2* | FIG. 1 and SEQ ID NO: 2 |
| RT4 | RT4 is similar to RT2. It comprises a thioredoxin-His patch tag in place of the His tag and linker in RT2. RT4 is as defined at SEQ ID NO: 69. |
| RT7 | Superscript II ™ (see Genebank: ABI05879.1 SEQ ID NO: 70). RT7 has different mutations within the MMLV-RT sequence, a N-terminal sequence different from RT2's and a C-terminal extension in place of RT2's terminal amino acid T. |
| RT8 | Correspond to the mutation set from Superscript II ™ (RT7) plus the construct boundary and N- and C- terminal sequences of RT2, including N-terminal expression enhancement sequence. RT8 is as defined at SEQ ID NO: 71 |

To trial heterologous expression, plasmids encoding RT constructs and plasmids encoding chaperones were co-transformed into BL21 *E. coli* cells with a standard heat shock transformation protocol and grown on Luria-Bertani broth (LB)—agar plates supplemented with 50 μg/ml kanamycin (Kn) and 34 μg/ml chloramphenicol (Cm) overnight at 37° C. Individual colonies from these plates were picked and transferred to 5 ml of LB supplemented with Kn and Cm and grown at 37° C. and 220 revolutions per minute (rpm) shaking speed overnight. Overnight culture was inoculated at a ratio of 1:100 into various fresh media, including M9 media, terrific broth (TB) and LB, supplemented with Kn and Cm. These cultures were grown at 37° C. and 220 rpm. Growth was monitored with absorbance of light at 600 nM wavelength. Various trials allowed the optical density to reach between 0.5 $OD_{600\ nm}$ and 2.0 $OD_{600\ nm}$, before induction protocol commenced. For induction, cultures were either left at 37° C., or transferred to a lower temperature, allowed to grow an additional 20 minutes and then protein expression was induced with various concentrations of isopropyl β-d-1-thiogalactopyranoside (IPTG). When chaperone co-expression was performed, this was induced with 0.5-4 mg/ml L-arabinose and/or 1-10 ng/ml tetracycline. Cultures continued to grow for between 4 and 48 hours, prior to harvesting by centrifugation in table-top centrifuge. Harvested cell pellet was then resuspended each pellet in 50 μl resuspension buffer (20 mM HEPES pH 8, 300 mM NaCl, 10% glycerol +DNaseI, with optional 0.5% triton and lysozyme) per OD unit of cell pellet. Cells were lysed by seven cycles of freeze/thawing by iteratively flash freezing in liquid nitrogen and incubation a 37° C. water bath. Sample of full lysate was taken, and the remaining lysate was centrifuged at in the bench top microcentrifuge at 4° C. in the cold room to pellet the cell debris and insoluble material. The pellet was discarded and the supernatant kept as representative of the soluble fraction of cell contents. Samples of 15 μl of each soluble fraction and 5 μl of selected whole cell lysates were mixed with SDS loading buffer and subject to denaturing gel electrophoresis using 10% polyacrylamide SDS gels.

Figure 4:
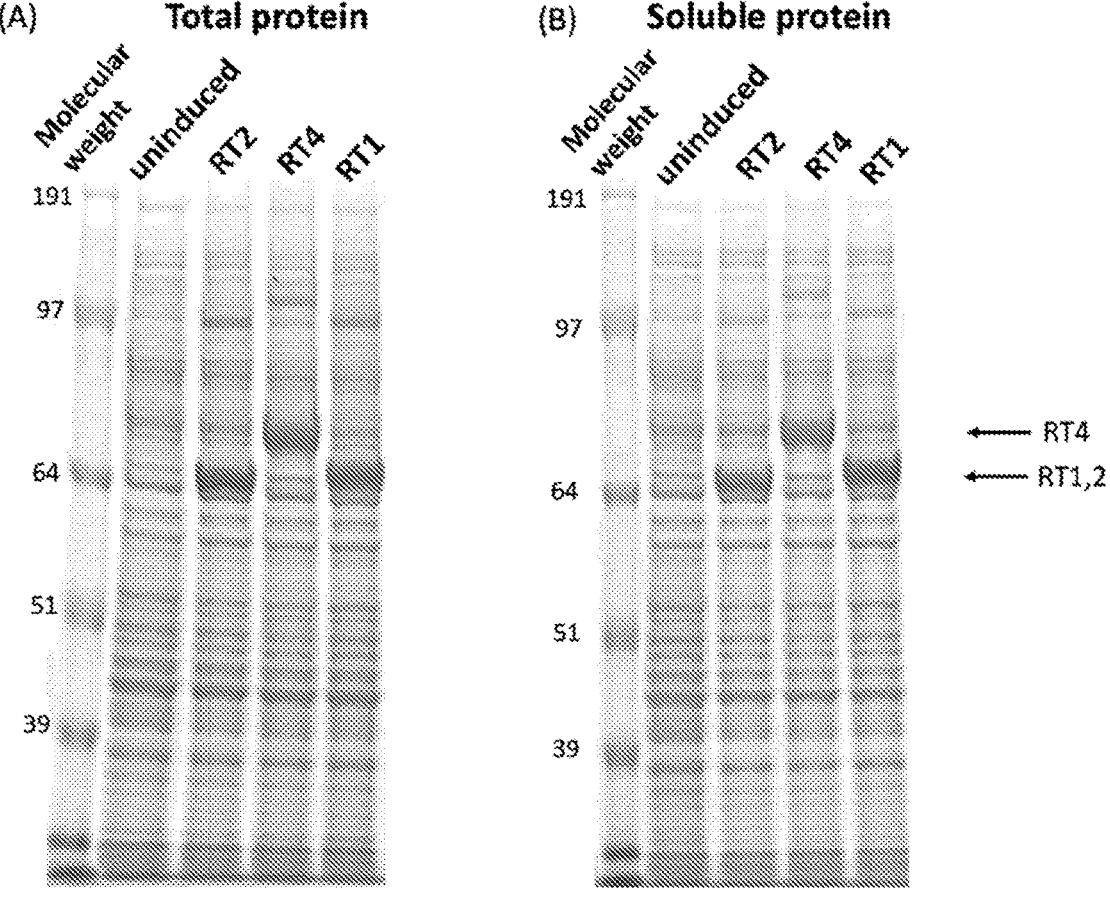
FIG. 4 is a panel with pictures showing the expression levels of total protein in (A) and soluble protein in (B) of using RT2, in comparison with RT4, which has a large expression tag, and RT1 which is reported to become unstable and precipitate during purification.

The results of the expression trials show that RT2 can be expressed at very high levels of soluble protein (FIG. 3). The levels of soluble protein are much higher (~8 fold more) than RT7 (Superscript II™) higher (~4 fold more) than RT8 (which contains the mutations of Superscript II™ combined with the construct boundary and tag-linker/expression enhancement sequence features of RT2) (FIG. 3). Thus RT2 has a substantial advantage over RT7 and RT8 (FIG. 2). Furthermore, the increased relative soluble expression of RT8 (FIG. 2 panel A, second from left lane of gel) compared to RT7 (FIG. 2 panel B, right lane of gel) show that the construct boundary and tag-linker/expression enhancement sequence do enhance soluble expression of reverse transcriptase constructs. In addition, the expression level is comparable to RT4, which includes a thioredoxin-His patch tag, included in as an attempt to increase the expression levels of soluble protein (FIG. 4). It is a major advantage to dispense with the thioredoxin-His patch tag, as it is much larger than the EES/tag-linker combination in RT2, and is known to affect protein activity if not removed by proteolytic cleavage. Thus RT2 has a substantial advantage over RT4 (FIG. 2). RT2 expression is comparable to RT1, the construct reported in Chen et al. (supra). RT1 has been as reported to be only a transiently stable construct, which precipitates unless cleaved by enterokinase (FIG. 4).

Figure 5:
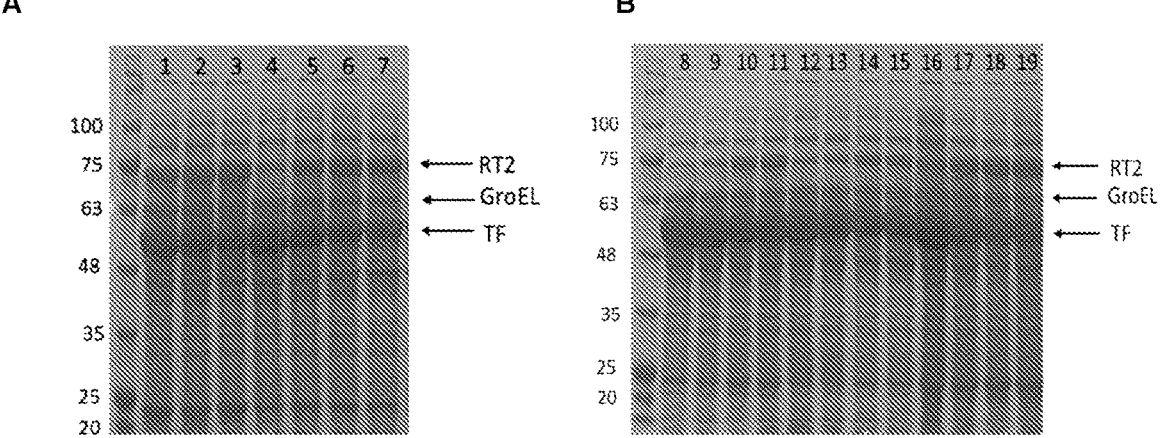
FIG. 5A is a panel with a picture showing expression of RT2 with 28° C. induction temperature, wherein lanes 1: 28° C., 0.05 mM IPTG, overnight, LB; 2: 28° C., 0.6 mM IPTG, overnight, LB; 3: 28° C., 1 mM IPTG, overnight, LB; 4: 28° C., 0 mM IPTG, overnight, TB; 5: 28° C., 0.05 mM IPTG, overnight, TB; 6: 28° C., 0.6 mM IPTG, overnight, TB; and 7: 28° C., 1 mM IPTG, overnight, TB.
FIG. 5B is a panel with a picture showing expression of RT2 with 16° C. induction temperature, wherein lanes 8: 16° C., 0 mM IPTG, overnight, LB; 9: 16° C., 0.05 mM IPTG, overnight, LB; 10: 16° C., 0.6 mM IPTG, overnight, LB; 11: 16° C., 1 mM IPTG, overnight, LB; 12: 16° C., 0 mM IPTG, overnight, TB; 13: 16° C., 0.05 mM IPTG, overnight, TB; 14: 16° C., 0.6 mM IPTG, overnight, TB; 15:16° C., 1 mM IPTG, overnight, TB; 16:16° C., 0 mM IPTG, overnight×2, TB; 17: 16° C., 0.05 mM IPTG, overnight×2, TB; 18: 16° C., 0.6 mM IPTG, overnight×2, TB; and 19: 16° C., 1 mM IPTG, overnight×2, TB.

Media, induction temperature and strength of induction signal can influence the soluble protein expression levels. It was therefore investigated whether RT2 expression was influenced by these factors (see FIG. 5). All three factors did influence the soluble protein expression levels, with several combinations yielding high soluble RT2 expression.

Figure 6:
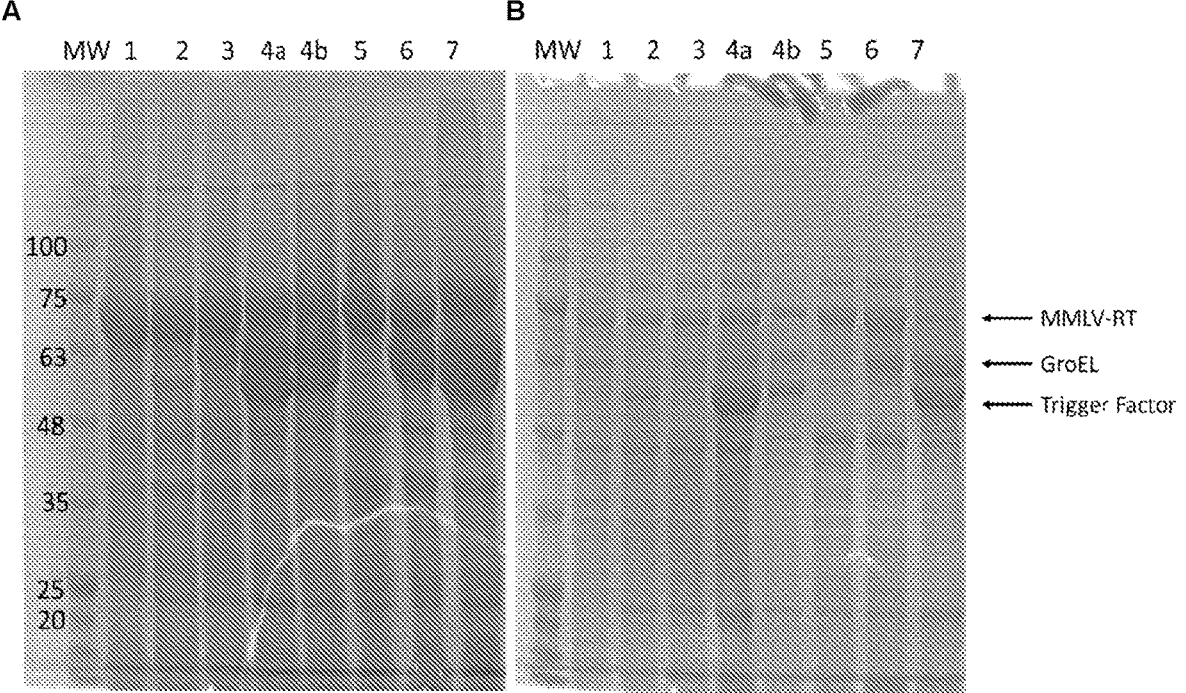
FIG. 6 is a panel with pictures showing in (A) total protein and in (B) soluble protein corresponding to the expression of RT2 with and without co-induction of chaperone proteins, and of RT7 with chaperones, wherein lanes 1: RT2+no chaperone; 2: RT2+TF; 3: RT2+GroEL-GroES; 4a: RT2+TF-GroEL-GroES (with Triton X100™ in the lysis buffer); 4b: RT2+TF-GroEL-GroES (no Triton X100™ in the lysis buffer); 5: RT2+DnaK-DnaJ-GrpE; 6: RT2+DnaK-DnaJ-GrpE-GroEL-GroES; and 7: RT7+TF and GroEL-GroES.

As provided herewith, RT1, the construct reported in Chen et al. (supra), not only was reported to be only transiently stable (precipitating in gentle buffer conditions), but also requires co-expression of chaperones for high soluble expression. Co-expression of chaperones for high soluble expression is unfavorable for several reasons, as it is indicative of a non-robust protein and of protein folding, adds components (extra plasmids) and variables (timing and level of induction) to the expression protocol, and necessitates potential licensing. It was therefore investigated whether RT2 could be expressed in soluble form in the absence of heterologous chaperone expression. The protocol as described hereinabove was repeated in the absence of co-transformation of chaperone-encoding plasmid and without Cm, L-arabinose or tetracycline supplementation to the media. FIG. 6 shows that RT2 can be expressed at high levels in the absence of chaperone. The total soluble RT2 is decreased by a modest proportion, but the modest decrease is worthwhile in the face of the negative factors that accompany co-expression of chaperone.

Figure 7:
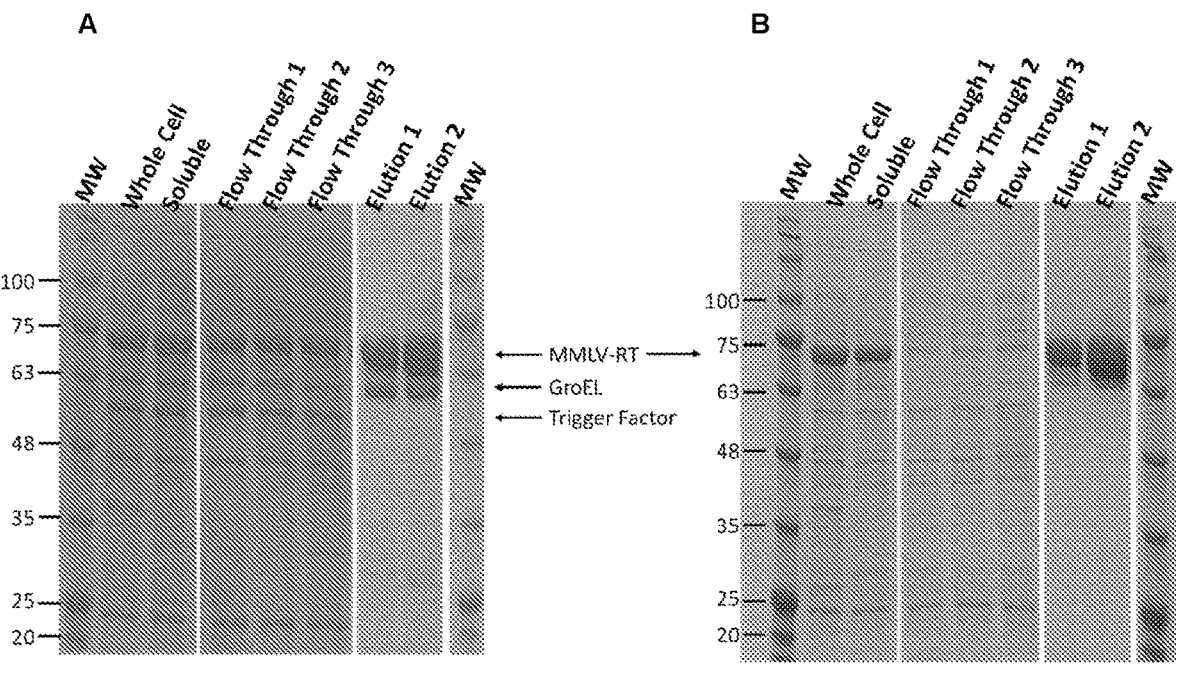
FIG. 7 is a panel with pictures showing the expression of RT2, in (A) with co-induction of chaperone proteins or in (B) without co-induction of chaperone proteins. Lanes labelled "Flow Through" shows that expression without chaperone proteins results in higher proportion of RT2 captured by nickel affinity column.

Furthermore, preforming nickel affinity chromatography of the sample of RT2 expressed in absence and presence of chaperones shows that the expression of RT2 without co-induction of chaperone proteins results in higher proportion of RT2 captured by nickel affinity column (FIG. 7). Thus, RT2 is advantageously expressed in the absence of chaperones, contrary to RT1 for example (FIG. 2).

Having shown that RT2 possesses major advantages (FIG. 2) over other constructs in soluble expression, an optimized expression and purification protocol is provided to obtain large amounts of pure, active RT2. For this, the following buffers were used:

Buffer RT-A: 20 mM HEPES pH 8, 300 mM NaCl, 20 mM imidazole, 0.5% Triton X100™, 10% glycerol, 1 mM DTT;

Buffer RT-B: 20 mM HEPES pH 8, 2 M NaCl, 0.5% Triton X100™, 10% glycerol, 1 mM DTT;

Buffer RT-C: 20 mM HEPES pH 8, 300 mM NaCl, 250 mM imidazole, 0.5 % Triton X100™, 10% glycerol, 1 mM DTT;

Buffer RT-D: 20 mM HEPES pH 8, 10% glycerol, 1 mM DTT; and

Buffer RT-E: 20 mM HEPES pH 8, 500 mM NaCl 10% glycerol, 1 mM DTT.

For expression (or "upstream processing"; USP) in flasks, the protocol begins with a fresh transformation of RT2 plasmid: a single aliquot of BL21 (DE3) competent cells was transformed with 1 μl of RT2 plasmid. The transformed cells were plated on LB-agar plates supplemented with 50 μg/ml kanamycin. It is understood that transformation will not be necessary if starting from a research cell bank (RCB). A culture was inoculated overnight at a scale of 10 ml LB-Kn (50 μg/ml) per liter of culture that was later used for USP and grew at 37° C., 220 rpm overnight. Next, 10 ml of overnight culture was inoculated overnight into 1 L of terrific broth (TB)-Kn (50 μg/ml) in 2 L baffled flasks, and grew at 37° C., 220 rpm until the OD600 is approximately 1, which typically takes 2.5-3 h. At that point, the culture growth temperature was shifted to 16° C. and allowed to continue to grow for a further hour. Thereafter, induction of expression was performed by addition of IPTG to 1 mM final (1 ml of a 1 M stock added to each liter or culture).

Cells were harvested by centrifugation, supernatant discarded and cell pellet stored at −80° C. prior to downstream processing (DSP).

For DSP, cells were resuspended in 10 ml of buffer RT-A supplemented with 1 mg/ml lysozyme and a 1 mg of DNaseI per unit OD600. Cells were lysed by sonication using 5 minutes total protocol with pulsing of 10 seconds on, 20 seconds off at 50% amplitude. Lysate was cleared by centrifugation at 20,000 rpm for 30 minutes in JA25.50 rotor at 4° C., and supernatant was harvested for subsequent steps.

For nickel affinity chromatography, supernatant was loaded onto a 1×5 ml HisTrap™ IMAC FF equilibrated in buffer RT-A. The column was next washed with buffer RT-A until the UV traces returns to the baseline, which requires around ~20 column volumes (CV) of washing. A high salt wash was performed by applying 3 CV of buffer RT-B, and then the column is re-equilibrated into buffer RT-A. RT2 was eluted with a 50 ml gradient to buffer RT-C, and an SDS-PAGE gel run to confirm which fractions contain RT2.

Tobacco etch virus protease (TEV) digestion: Optionally, the polyhistidine tag of RT2 can be removed with treatment of TEV. When investigating merits of removing the tag against leaving the tag attached to RT2, 1 mg of TEV was incubated with ~20 mg of RT2 and incubated in dialysis membrane 1L of buffer containing 20 mM HEPES pH 8, 150 mM NaCl, 0.1% Triton X-100, 5% glycerol at 4° C., overnight. The next morning this sample was applied to a 1×5 ml HisTrap™ IMAC FF equilibrated in buffer RT-A, and the flow-through collected for further steps.

For anion exchange chromatography, pooled fractions of RT2 from nickel affinity were diluted in a 1:1 ratio with buffer RT-D, and the resulting solution was filtered to remove potential precipitate, using a 250 ml SteriCup™ with 0.22 μm pore size. The resulting solution was applied to 5 ml Q HP column equilibrated in 30% buffer RT-E (i.e. 150 mM NaCl). Fractions were collected and an SDS-PAGE gel run to confirm which flow-through fractions contain RT2.

Figure 8:
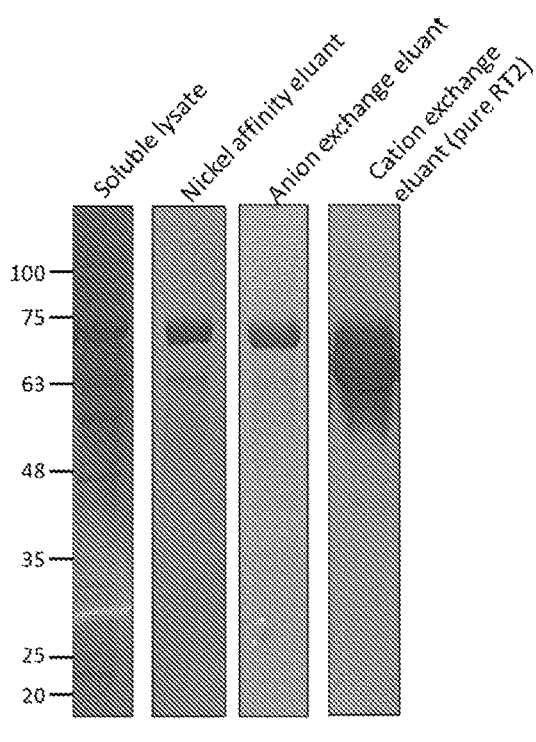
FIG. 8 is a panel with pictures showing that purification of RT2 without co-induction of chaperone proteins gives highly pure protein.

For cation exchange chromatography, pooled fractions of RT2 from anion exchange chromatography applied to a 5 ml SP HP column equilibrated in 70% buffer RT-D/30% buffer RT-E. The column was washed with 20 CV of 70% buffer RT-D/30% buffer RT-E (to complete the removal of Triton X100™) and then eluted protein with a 100 ml gradient from 70% buffer RT-D/30% buffer RT-E to 100% buffer RT-E. RT2 elutes at around 40% buffer RT-D/60% buffer RT-E. Fractions were collected and an SDS-PAGE gel run to confirm which fractions contain RT2. RT2 was concentrated using a 30 kDa MWCO Amicon Ultra™, aliquoted and flash frozen by submersion in liquid nitrogen, and stored at −80° C. FIG. 8 shows that the described purification protocol produces extremely pure protein. Remarkably, the final yield of this highly purified protein is greater or equal to 120 mg per liter of flask-grown culture medium. This is an outstanding amount. In comparison, Chen et al. (supra) reported 21 mg per liter of flask-grown culture medium, and all other publications known in the art report in the order of ~2 mg per liter of flask-grown culture medium.

RT2 sample in which the poly-histidine tag had been retained and RT2 sample in which the poly-histidine tag had been removed by TEV cleavage behaved identically in solution, and did not precipitate in the way reported by Chen et al. (supra) for their construct. Furthermore, RT2 sample in which the poly-histidine tag had been retained, and RT2 sample in which the poly-histidine tag had been removed by TEV cleavage retained equal activity. Therefore, RT2 has a major advantage over RT1 in that TEV cleavage is not necessary. This can save up to one million dollars per large-scale DSP, as GMP-quality TEV protease and the steps in which it is used, can cost this amount.

Example 2: Performance of RT2 vs. Commercially Purchased RT Enzymes in RT-qPCR The RT2 provided herein can be used in RT-qPCR reactions showing a signal based on degradation of a probe which contains a fluorescent dye and a quencher.

As shown in FIG. 9A and FIG. 9B, RT2 was compared with commercial RT enzymes. For FIG. 9A twenty microliter RT-qPCR reactions were set with glycerol at 15 % (vol/vol), Tris-HCl at pH 8 and 90 mM, BSA at 1000 µg/mL, $(NH_4)2SO4$ at 18 mM, $MgSO_4$ at 2.4 mM, DTT at 2.5 mM, KCl at 40 mM, tetrapropylammonium hydroxide at 15 mM, DMSO at 2% (vol/vol), dNTPs (dATP, dUTP, dTTP, dGTP, dCTP) at 0.2 mM, polyinosinic acid at 0.1 µg/µl, Triton™ X-100 at 0.25% (vol/vol), IGEPAL™ CA-630 at 0.25% (vol/vol), hotstart DNA oligomer HS2 at 125 nM, DNA Polymerase at 0.25 U/µl, Uracil DNA glycosylase at 0.01 U/µl, RNAse inhibitor protein at 1 U/µl, Corman™ E gene primers (Sarbeco_F Forward Primer—IDT Catalog number 10006889, E_Sarbeco_R Reverse Primer—IDT Catalog number 10006891) at 600 nM and Corman™ E gene probe (E_Sarbeco_P1 Probe—Catalog number 10006893 DNA) at 200 nM, template from ATCC (ATCC-VR3276SD—Quantitative Synthetic SARS-CoV-2 RNA: ORF, E, N (ATCC® VR-32765D™) diluted 1:100 (resulting in ~28,000 template RNA molecules per reaction) and 10 Wul of a commercial RT (Sigma RT: M-MLV Reverse Transcriptase, M1427-5KU; Promega RT: M-MLV Reverse Transcriptase, M170A; Invitrogen RT: ThermoFisher Superscript™ II 18064022), or 10 U/ul RT2 (estimated specific activity of 1,000,000 U/mg). For FIG. 9B, reactions were set as described for FIG. 9A, except template from ATCC was diluted 1:50,000 (resulting in ~55 template RNA molecules per reaction). The thermocycling parameters are one cycle of 53° C. for 10 minutes, followed by one cycle of 95° C. for 2 minutes, followed by forty-five cycles of 95° C. for 15 seconds and 60° C. for 30 seconds, followed by one cycle of 60° C. for 30 seconds, in a Biorad™ thermocycler. FIG. 9A and B shows RT2 to be as good or better in activity (allowing the RT-qPCR to be more sensitive, with lower cycle threshold (Ct values)) than other RTs.

Figure 10:
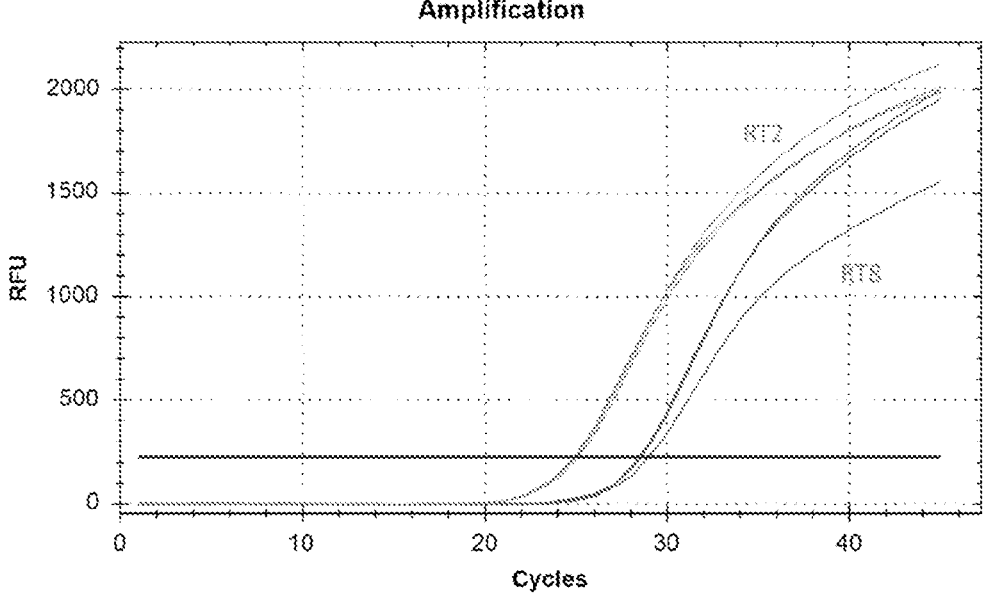
FIG. 10 is a line graph showing the performance of RT2 (upper lines) vs. RT8 (lower lines) in RT-qPCR. RT-qPCR reactions used Corman™ E gene primers at 400 nM and Corman™ E gene probe at 200 nM, to amplify and quantify template from ATCC diluted by 1:100 (resulting in ~28,000 template RNA molecules per reaction).

For FIG. 10, twenty microliter RT-qPCR reactions were set with RT at 15 U/µL, UDG at 0.01 U/µL, RNAse inhibitor at 1 U/µL, Taq DNA polymerase at 0.375 U/µL, dNTPs at 0.2 mM, BSA at 1 mg/mL, Tris-SO₄ pH 8 at 60 mM, $(NH_4)_2SO_4$ at 18 mM, $MgSO_4$ at 2.4 mM, DTT at 2.5 mM, KCl at 40 mM, DMSO at 2%, Corman™ E gene primers at 400 nM and Corman™ E gene probe at 200 nM. The thermocycling parameters are one cycle of 53° C. for 10 minutes, followed by one cycle of 95° C. for 2 minutes, followed by forty-five cycles of 95° C. for 15 seconds and 60° C. for 30 seconds, followed by one cycle of 60° C. for 30 seconds, in a Biorad™ thermocycler. FIG. 10 shows that RT2 has better in activity (allowing the RT-qPCR to be more sensitive with lower Ct values), and more consistent than other RTs.

As can be appreciated, the present results demonstrate that RT2 may allow facile protocols for its high purity purification. This variant possesses high specific activity in reaction which produces DNA molecules using a single-stranded RNA template. This variant comprises high activity level and is a useful component in one-step reverse transcription quantitative polymerase chain reaction.

Headings are included herein for reference and to aid in locating certain sections. These headings are not intended to limit the scope of the concepts described therein, and these concepts may have applicability in other sections throughout the entire specification. Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise. Thus, for example, reference to "an amino acid sequence " includes one or more of such amino acids and reference to "the method" includes reference to equivalent steps and methods known to those of ordinary skill in the art that could be modified or substituted for the methods described herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contains certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

---

The invention claimed is:

1. A protein construct of Moloney murine leukemia virus reverse transcriptase (MMLV-RT), comprising:

a mutant Moloney murine leukemia virus reverse transcriptase (MMLV) mature protein sequence with at least 99% sequence identity to SEQ ID NO: 2, and having an expression enhancement sequence at the N-terminus of said mutant MMLV mature protein sequence, wherein the expression enhancement sequence has one of the following sequences:

```
                          (SEQ ID NO: 64)
MGHHHHHHHHPDLGTGSENLYFQ;

(SEQ ID NO: 65)
MGHHHHHHHHPDLGTGSENLYFQG;
``` or

```
                          (SEQ ID NO: 66)
MGHHHHHHHHPDLGTGSENLYFQS.
```

2. A reverse transcription reaction kit for performing a reverse transcription reaction, comprising any one of the protein constructs of claim 1 and one or more of a ready-to-use reagent mixture for reverse transcription polymerase chain reaction (RT-PCR), sample collecting tube(s), reaction tube(s), microplate(s), buffer for the homogenization of sample(s), incubation buffer(s), assay buffer(s), fluorescent and/or luminogenic detection materials, desalting column(s), purified control purified RNA or cDNA and a user manual or instructions.

* * * * *

SEQUENCE LISTING

<160> NUMBER OF SEQ ID NOS: 71

<210> SEQ ID NO 1
<211> LENGTH: 2082
<212> TYPE: DNA
<213> ORGANISM: Artificial Sequence
<220> FEATURE:
<223> OTHER INFORMATION: Sequence is completely synthesized

<400> SEQUENCE: 1

-continued

```
atgggtcatc atcatcatca tcatcaccac ccggacctgg gtaccggtag cgagaacctg        60
tactttcagg gtcaaccgct gcaggtgctg accctgaaca tcgaggatga acaccgtctg       120
cacgagacca gcaaggaacc ggacgttagc ctgggtagca cctggctgag cgatttcccg       180
caggcgtggg cggaaaccgg tggcatgggt ctggcggtgc gtcaagcgcc gctgatcatt       240
ccgctgaagg cgaccagcac cccggttagc atcaaacagt acccgatgag ccaaaaggcg       300
cgtctgggta tcaaaccgca cattcagcgt ctgctggacc aaggcattct ggtgccgtgc       360
caaagcccgt ggaacacccc gctgctgccg gtgaagaaac cgggcaccaa cgactatcgt       420
ccggttcagg atctgcgtga ggtgaacaag cgtgttgaag atatccaccc gaccgtgccg       480
aacccgtaca acctgctgag cggtctgccg ccgagccatc agtggtatac cgttctggac       540
ctgaaagatg cgttcttttg cctgcgtctg catccgacca gccagccgct gtttgcgttt       600
gagtggcgtg acccggaaat gggtattagc ggtcagctga cctggacccg tctgccgcaa       660
ggctttaaaa acagcccgac cctgtttgat gaggcgctgc accgtgacct ggcggatttt       720
cgtatccagc acccggatct gattctgctg caatacgttg acgatctgct gctggcggcg       780
accagcgaac tggattgcca gcaaggtacc cgtgcgctgc tgcagaccct gggtaacctg       840
ggctatcgtg cgagcgcgaa gaaagcgcaa atctgccaga gcaagtgaa atacctgggt       900 tatctgctga agagggtca gcgttggctg accgaggcgc gtaaggaaac cgttatgggt       960
cagccgaccc cgaaaacccc gcgtcaactg cgtcgttttc tgggtaccgc gggcttctgc      1020 cgtctgtttta ttccgggttt tgcggagatg cggcgccgc tgtacccgct gaccaaaaacc      1080 ggtaccctgt tcaactgggg cccggaccag caaaaggcgt atcaggaaat taaacaagcg      1140
ctgctgaccg cgccggcgct gggtctgccg gacctgacca gccgttcga gctgtttgtg      1200 gatgaaaagc agggttacgc gaaaggcgtt ctgacccaaa aactgggtcc gtggcgtcgt      1260
ccggtggcgt atctgagcaa gaaactggac ccggttgcgg cgggttggcc gccatgcctg      1320
cgtatggtgg cggcgatcgc ggttctgacc aaggatgcgg gtaaactgac catgggtcag      1380
ccgctggtga ttggtgcgcc gcacgcggtg gaagcgctgg ttaagcaacc gccggaccgt      1440
tggctgagca aagcgcgtat gacccactac caggcgctgc tgctggacac cgatcgtgtt      1500
caatttggtc cggtggttgc gctgaacccg gcgaccctgc tgccgctgcc ggaggaaggt      1560
ctgcagcaca actgcctgga tattctggcg gaggcgcatg gtacccgtcc ggacctgacc      1620
gatcaaccgc tgccggacgc ggatcacacc tggtatacca acggtagcag cctgctgcag      1680
gaaggtcagc gtaaagcggg tgcggcggtg accaccgaga ccgaagttat ctgggcgaag      1740
gcgctgccgg cgggtaccag cgcgcagcgt gcggagctga ttgcgctgac ccaagcgctg      1800
aagatggcgg aaggcaagaa actgaacgtg tacaccgaca gccgttatgc gtttgcgacc      1860
gcgcacatcc acggcgagat ttaccgtcgt cgtggtctgc tgaccagcga gggcaaggaa      1920
atcaagaaca aggatgaaat cctggcgctg ctgaaggcgc tgttcctgcc gaaacgtctg      1980
agcatcattc actgcccggg tcaccagaaa ggtcacagcg cggaggcgcg tggtaaccgt      2040
atggcggacc aagcggcgcg taaagcggcg attaccgaaa cc                        2082
```

<210> SEQ ID NO 2
<211> LENGTH: 694
<212> TYPE: PRT
<213> ORGANISM: Artificial Sequence
<220> FEATURE:
<223> OTHER INFORMATION: sequence is completely synthesized

```
<400> SEQUENCE: 2

Met Gly His His His His His His His Pro Asp Leu Gly Thr Gly
1               5                   10                  15

Ser Glu Asn Leu Tyr Phe Gln Gly Gln Pro Leu Gln Val Leu Thr Leu
            20                  25                  30

Asn Ile Glu Asp Glu His Arg Leu His Glu Thr Ser Lys Glu Pro Asp
            35                  40                  45

Val Ser Leu Gly Ser Thr Trp Leu Ser Asp Phe Pro Gln Ala Trp Ala
    50                  55                  60

Glu Thr Gly Gly Met Gly Leu Ala Val Arg Gln Ala Pro Leu Ile Ile
65                  70                  75                  80

Pro Leu Lys Ala Thr Ser Thr Pro Val Ser Ile Lys Gln Tyr Pro Met
                85                  90                  95

Ser Gln Lys Ala Arg Leu Gly Ile Lys Pro His Ile Gln Arg Leu Leu
            100                 105                 110

Asp Gln Gly Ile Leu Val Pro Cys Gln Ser Pro Trp Asn Thr Pro Leu
            115                 120                 125

Leu Pro Val Lys Lys Pro Gly Thr Asn Asp Tyr Arg Pro Val Gln Asp
    130                 135                 140

Leu Arg Glu Val Asn Lys Arg Val Glu Asp Ile His Pro Thr Val Pro
145                 150                 155                 160

Asn Pro Tyr Asn Leu Leu Ser Gly Leu Pro Pro Ser His Gln Trp Tyr
                165                 170                 175

Thr Val Leu Asp Leu Lys Asp Ala Phe Phe Cys Leu Arg Leu His Pro
                180                 185                 190

Thr Ser Gln Pro Leu Phe Ala Phe Glu Trp Arg Asp Pro Glu Met Gly
            195                 200                 205

Ile Ser Gly Gln Leu Thr Trp Thr Arg Leu Pro Gln Gly Phe Lys Asn
    210                 215                 220

Ser Pro Thr Leu Phe Asp Glu Ala Leu His Arg Asp Leu Ala Asp Phe
225                 230                 235                 240

Arg Ile Gln His Pro Asp Leu Ile Leu Leu Gln Tyr Val Asp Asp Leu
                245                 250                 255

Leu Leu Ala Ala Thr Ser Glu Leu Asp Cys Gln Gln Gly Thr Arg Ala
            260                 265                 270

Leu Leu Gln Thr Leu Gly Asn Leu Gly Tyr Arg Ala Ser Ala Lys Lys
            275                 280                 285

Ala Gln Ile Cys Gln Lys Gln Val Lys Tyr Leu Gly Tyr Leu Leu Lys
    290                 295                 300

Glu Gly Gln Arg Trp Leu Thr Glu Ala Arg Lys Glu Thr Val Met Gly
305                 310                 315                 320

Gln Pro Thr Pro Lys Thr Pro Arg Gln Leu Arg Arg Phe Leu Gly Thr
                325                 330                 335

Ala Gly Phe Cys Arg Leu Phe Ile Pro Gly Phe Ala Glu Met Ala Ala
            340                 345                 350

Pro Leu Tyr Pro Leu Thr Lys Thr Gly Thr Leu Phe Asn Trp Gly Pro
            355                 360                 365

Asp Gln Gln Lys Ala Tyr Gln Glu Ile Lys Gln Ala Leu Leu Thr Ala
    370                 375                 380

Pro Ala Leu Gly Leu Pro Asp Leu Thr Lys Pro Phe Glu Leu Phe Val
385                 390                 395                 400

Asp Glu Lys Gln Gly Tyr Ala Lys Gly Val Leu Thr Gln Lys Leu Gly
                405                 410                 415
```

```
Pro Trp Arg Arg Pro Val Ala Tyr Leu Ser Lys Lys Leu Asp Pro Val
            420                 425                 430

Ala Ala Gly Trp Pro Pro Cys Leu Arg Met Val Ala Ala Ile Ala Val
            435                 440                 445

Leu Thr Lys Asp Ala Gly Lys Leu Thr Met Gly Gln Pro Leu Val Ile
            450                 455                 460

Gly Ala Pro His Ala Val Glu Ala Leu Val Lys Gln Pro Pro Asp Arg
465                 470                 475                 480

Trp Leu Ser Lys Ala Arg Met Thr His Tyr Gln Ala Leu Leu Leu Asp
                485                 490                 495

Thr Asp Arg Val Gln Phe Gly Pro Val Val Ala Leu Asn Pro Ala Thr
            500                 505                 510

Leu Leu Pro Leu Pro Glu Glu Gly Leu Gln His Asn Cys Leu Asp Ile
            515                 520                 525

Leu Ala Glu Ala His Gly Thr Arg Pro Asp Leu Thr Asp Gln Pro Leu
            530                 535                 540

Pro Asp Ala Asp His Thr Trp Tyr Thr Asn Gly Ser Ser Leu Leu Gln
545                 550                 555                 560

Glu Gly Gln Arg Lys Ala Gly Ala Ala Val Thr Thr Glu Thr Glu Val
                565                 570                 575

Ile Trp Ala Lys Ala Leu Pro Ala Gly Thr Ser Ala Gln Arg Ala Glu
                580                 585                 590

Leu Ile Ala Leu Thr Gln Ala Leu Lys Met Ala Glu Gly Lys Lys Leu
                595                 600                 605

Asn Val Tyr Thr Asp Ser Arg Tyr Ala Phe Ala Thr Ala His Ile His
            610                 615                 620

Gly Glu Ile Tyr Arg Arg Arg Gly Leu Leu Thr Ser Glu Gly Lys Glu
625                 630                 635                 640

Ile Lys Asn Lys Asp Glu Ile Leu Ala Leu Leu Lys Ala Leu Phe Leu
                645                 650                 655

Pro Lys Arg Leu Ser Ile Ile His Cys Pro Gly His Gln Lys Gly His
                660                 665                 670

Ser Ala Glu Ala Arg Gly Asn Arg Met Ala Asp Gln Ala Ala Arg Lys
                675                 680                 685

Ala Ala Ile Thr Glu Thr
    690
```

```
<210> SEQ ID NO 3
<211> LENGTH: 2106
<212> TYPE: DNA
<213> ORGANISM: Artificial Sequence
<220> FEATURE:
<223> OTHER INFORMATION: Sequence is completely synthesized

<400> SEQUENCE: 3
atgggtcatc atcatcatca tcatcaccac ccggacctgg gtaccggtag cgagaacctg      60
tactttcagg gtcaaccgct gcaggtgctg accctgaaca tcgaggatga acaccgtctg     120
cacgagacca gcaaggaacc ggacgttagc ctgggtagca cctggctgag cgatttcccg     180
caggcgtggg cggaaaccgg tggcatgggt ctggcggtgc gtcaagcgcc gctgatcatt     240
ccgctgaagg cgaccagcac cccggttagc atcaaacagt acccgatgag ccaaaaggcg     300
cgtctgggta tcaaaccgca cattcagcgt ctgctggacc aaggcattct ggtgccgtgc     360
caaagcccgt ggaacacccc gctgctgccg gtgaagaaac cgggcaccaa cgactatcgt     420
```

```
ccggttcagg atctgcgtga ggtgaacaag cgtgttgaag atatccaccc gaccgtgccg    480
aacccgtaca acctgctgag cggtctgccg ccgagccatc agtggtatac cgttctggac    540
ctgaaagatg cgttcttttg cctgcgtctg catccgacca gccagccgct gtttgcgttt    600
gagtggcgtg acccggaaat gggtattagc ggtcagctga cctggacccg tctgccgcaa    660
ggctttaaaa acagcccgac cctgtttgat gaggcgctgc accgtgacct ggcggatttt    720
cgtatccagc acccggatct gattctgctg caatacgttg acgatctgct gctggcggcg    780
accagcgaac tggattgcca gcaaggtacc cgtgcgctgc tgcagaccct gggtaacctg    840
ggctatcgtg cgagcgcgaa gaaagcgcaa atctgccaga gcaagtgaa atacctgggt    900 tatctgctga aagagggtca gcgttggctg accgaggcgc gtaaggaaac cgttatgggt    960
cagccgaccc cgaaaacccc gcgtcaactg cgtcgttttc tgggtaccgc gggcttctgc    1020 cgtctgtttta ttccgggttt tgcggagatg gcggcgccgc tgtacccgct gaccaaaacc    1080
ggtaccctgt tcaactgggg cccggaccag caaaaggcgt atcaggaaat taaacaagcg    1140
ctgctgaccg cgccggcgct gggtctgccg gacctgacca gccgttcga gctgtttgtg    1200 gatgaaaagc agggttacgc gaaaggcgtt ctgacccaaa aactgggtcc gtggcgtcgt    1260
ccggtggcgt atctgagcaa gaaactggac ccggttgcgg cgggttggcc gccatgcctg    1320
cgtatggtgg cggcgatcgc ggttctgacc aaggatgcgg gtaaactgac catgggtcag    1380
ccgctggtga ttggtgcgcc gcacgcggtg gaagcgctgg ttaagcaacc gccggaccgt    1440
tggctgagca agcgcgtat gacccactac caggcgctgc tgctggacac cgatcgtgtt    1500
caatttggtc cggtggttgc gctgaacccg gcgaccctgc tgccgctgcc ggaggaaggt    1560
ctgcagcaca actgcctgga tattctggcg gaggcgcatg gtacccgtcc ggacctgacc    1620
gatcaaccgc tgccggacgc ggatcacacc tggtatacca acggtagcag cctgctgcag    1680
gaaggtcagc gtaaagcggg tgcggcggtg accaccgaga ccgaagttat ctgggcgaag    1740
gcgctgccgg cgggtaccag cgcgcagcgt gcggagctga ttgcgctgac caagcgctg    1800 aagatggcgg aaggcaagaa actgaacgtg tacaccgaca gccgttatgc gtttgcgacc    1860
gcgcacatcc acggcgagat ttaccgtcgt cgtggtctgc tgaccagcga gggcaaggaa    1920
atcaagaaca aggatgaaat cctggcgctg ctgaaggcgc tgttcctgcc gaaacgtctg    1980
agcatcattc actgcccggg tcaccagaaa ggtcacagcg cggaggcgcg tggtaaccgt    2040
atggcggacc aagcggcgcg taaagcggcg attaccgaaa ccccagacac ctctaccctc    2100
ctcata                                                                   2106
```

```
<210> SEQ ID NO 4
<211> LENGTH: 702
<212> TYPE: PRT
<213> ORGANISM: Artificial Sequence
<220> FEATURE:
<223> OTHER INFORMATION: sequence is completely synthesized

<400> SEQUENCE: 4

Met Gly His His His His His His His His Pro Asp Leu Gly Thr Gly
1               5                   10                  15

Ser Glu Asn Leu Tyr Phe Gln Gly Gln Pro Leu Gln Val Leu Thr Leu
            20                  25                  30

Asn Ile Glu Asp Glu His Arg Leu His Glu Thr Ser Lys Glu Pro Asp
        35                  40                  45

Val Ser Leu Gly Ser Thr Trp Leu Ser Asp Phe Pro Gln Ala Trp Ala
    50                  55                  60
```

```
Glu Thr Gly Gly Met Gly Leu Ala Val Arg Gln Ala Pro Leu Ile Ile
65              70                  75                  80

Pro Leu Lys Ala Thr Ser Thr Pro Val Ser Ile Lys Gln Tyr Pro Met
                85                  90                  95

Ser Gln Lys Ala Arg Leu Gly Ile Lys Pro His Ile Gln Arg Leu Leu
            100                 105                 110

Asp Gln Gly Ile Leu Val Pro Cys Gln Ser Pro Trp Asn Thr Pro Leu
            115                 120                 125

Leu Pro Val Lys Lys Pro Gly Thr Asn Asp Tyr Arg Pro Val Gln Asp
    130                 135                 140

Leu Arg Glu Val Asn Lys Arg Val Glu Asp Ile His Pro Thr Val Pro
145                 150                 155                 160

Asn Pro Tyr Asn Leu Leu Ser Gly Leu Pro Pro Ser His Gln Trp Tyr
                165                 170                 175

Thr Val Leu Asp Leu Lys Asp Ala Phe Phe Cys Leu Arg Leu His Pro
                180                 185                 190

Thr Ser Gln Pro Leu Phe Ala Phe Glu Trp Arg Asp Pro Glu Met Gly
            195                 200                 205

Ile Ser Gly Gln Leu Thr Trp Thr Arg Leu Pro Gln Gly Phe Lys Asn
    210                 215                 220

Ser Pro Thr Leu Phe Asp Glu Ala Leu His Arg Asp Leu Ala Asp Phe
225                 230                 235                 240

Arg Ile Gln His Pro Asp Leu Ile Leu Leu Gln Tyr Val Asp Asp Leu
                245                 250                 255

Leu Leu Ala Ala Thr Ser Glu Leu Asp Cys Gln Gln Gly Thr Arg Ala
            260                 265                 270

Leu Leu Gln Thr Leu Gly Asn Leu Gly Tyr Arg Ala Ser Ala Lys Lys
            275                 280                 285

Ala Gln Ile Cys Gln Lys Gln Val Lys Tyr Leu Gly Tyr Leu Leu Lys
    290                 295                 300

Glu Gly Gln Arg Trp Leu Thr Glu Ala Arg Lys Glu Thr Val Met Gly
305                 310                 315                 320

Gln Pro Thr Pro Lys Thr Pro Arg Gln Leu Arg Arg Phe Leu Gly Thr
                325                 330                 335

Ala Gly Phe Cys Arg Leu Phe Ile Pro Gly Phe Ala Glu Met Ala Ala
            340                 345                 350

Pro Leu Tyr Pro Leu Thr Lys Thr Gly Thr Leu Phe Asn Trp Gly Pro
            355                 360                 365

Asp Gln Gln Lys Ala Tyr Gln Glu Ile Lys Gln Ala Leu Leu Thr Ala
    370                 375                 380

Pro Ala Leu Gly Leu Pro Asp Leu Thr Lys Pro Phe Glu Leu Phe Val
385                 390                 395                 400

Asp Glu Lys Gln Gly Tyr Ala Lys Gly Val Leu Thr Gln Lys Leu Gly
            405                 410                 415

Pro Trp Arg Arg Pro Val Ala Tyr Leu Ser Lys Lys Leu Asp Pro Val
            420                 425                 430

Ala Ala Gly Trp Pro Pro Cys Leu Arg Met Val Ala Ala Ile Ala Val
            435                 440                 445

Leu Thr Lys Asp Ala Gly Lys Leu Thr Met Gly Gln Pro Leu Val Ile
    450                 455                 460

Gly Ala Pro His Ala Val Glu Ala Leu Val Lys Gln Pro Pro Asp Arg
465                 470                 475                 480
```

-continued

```
Trp Leu Ser Lys Ala Arg Met Thr His Tyr Gln Ala Leu Leu Leu Asp
            485                 490                 495

Thr Asp Arg Val Gln Phe Gly Pro Val Val Ala Leu Asn Pro Ala Thr
            500                 505                 510

Leu Leu Pro Leu Pro Glu Glu Gly Leu Gln His Asn Cys Leu Asp Ile
            515                 520                 525

Leu Ala Glu Ala His Gly Thr Arg Pro Asp Leu Thr Asp Gln Pro Leu
        530                 535                 540

Pro Asp Ala Asp His Thr Trp Tyr Thr Asn Gly Ser Ser Leu Leu Gln
545                 550                 555                 560

Glu Gly Gln Arg Lys Ala Gly Ala Ala Val Thr Thr Glu Thr Glu Val
            565                 570                 575

Ile Trp Ala Lys Ala Leu Pro Ala Gly Thr Ser Ala Gln Arg Ala Glu
            580                 585                 590

Leu Ile Ala Leu Thr Gln Ala Leu Lys Met Ala Glu Gly Lys Lys Leu
            595                 600                 605

Asn Val Tyr Thr Asp Ser Arg Tyr Ala Phe Ala Thr Ala His Ile His
            610                 615                 620

Gly Glu Ile Tyr Arg Arg Arg Gly Leu Leu Thr Ser Glu Gly Lys Glu
625                 630                 635                 640

Ile Lys Asn Lys Asp Glu Ile Leu Ala Leu Leu Lys Ala Leu Phe Leu
            645                 650                 655

Pro Lys Arg Leu Ser Ile Ile His Cys Pro Gly His Gln Lys Gly His
            660                 665                 670

Ser Ala Glu Ala Arg Gly Asn Arg Met Ala Asp Gln Ala Ala Arg Lys
            675                 680                 685

Ala Ala Ile Thr Glu Thr Pro Asp Thr Ser Thr Leu Leu Ile
        690                 695                 700

<210> SEQ ID NO 5
<211> LENGTH: 21
<212> TYPE: PRT
<213> ORGANISM: Artificial Sequence
<220> FEATURE:
<223> OTHER INFORMATION: sequence is completely synthesized

<400> SEQUENCE: 5

Pro Asp Leu Gly Thr Gly Ser Glu Asn Leu Tyr Phe Gln Gly Gln Pro
1               5                   10                  15

Leu Gln Val Leu Thr
            20

<210> SEQ ID NO 6
<211> LENGTH: 21
<212> TYPE: PRT
<213> ORGANISM: Artificial Sequence
<220> FEATURE:
<223> OTHER INFORMATION: sequence is completely synthesized

<400> SEQUENCE: 6

His Phe Glu Gly Ser Gly Ala Gln Val Met Gly Pro Met Gly Gln Pro
1               5                   10                  15

Leu Gln Val Leu Thr
            20

<210> SEQ ID NO 7
<211> LENGTH: 21
<212> TYPE: PRT
<213> ORGANISM: Artificial Sequence
```

```
<220> FEATURE:
<223> OTHER INFORMATION: sequence is completely synthesized
<220> FEATURE:
<221> NAME/KEY: MISC_FEATURE
<222> LOCATION: (1)..(1)
<223> OTHER INFORMATION: Xaa1 can be represented by any amino acid of P,
      G, S, A or T
<220> FEATURE:
<221> NAME/KEY: MISC_FEATURE
<222> LOCATION: (2)..(2)
<223> OTHER INFORMATION: Xaa2 can be represented by any amino acid of D,
      E, N or Q
<220> FEATURE:
<221> NAME/KEY: MISC_FEATURE
<222> LOCATION: (3)..(3)
<223> OTHER INFORMATION: Xaa3 can be represented by any amino acid of G,
      A, V, L or I
<220> FEATURE:
<221> NAME/KEY: MISC_FEATURE
<222> LOCATION: (4)..(4)
<223> OTHER INFORMATION: Xaa4 can be represented by any amino acid of G,
      A, V, L or I
<220> FEATURE:
<221> NAME/KEY: MISC_FEATURE
<222> LOCATION: (5)..(5)
<223> OTHER INFORMATION: Xaa5 can be represented by any amino acid of S,
      C, T or M
<220> FEATURE:
<221> NAME/KEY: MISC_FEATURE
<222> LOCATION: (6)..(6)
<223> OTHER INFORMATION: Xaa6 can be represented by any amino acid of G,
      A, V, L or I
<220> FEATURE:
<221> NAME/KEY: MISC_FEATURE
<222> LOCATION: (7)..(7)
<223> OTHER INFORMATION: Xaa7 can be represented by any amino acid of S,
      C, T or M
<220> FEATURE:
<221> NAME/KEY: MISC_FEATURE
<222> LOCATION: (8)..(8)
<223> OTHER INFORMATION: Xaa8 can be represented by any amino acid of D,
      E, N or Q
<220> FEATURE:
<221> NAME/KEY: MISC_FEATURE
<222> LOCATION: (9)..(9)
<223> OTHER INFORMATION: Xaa9 can be represented by any amino acid of D,
      E, N or Q
<220> FEATURE:
<221> NAME/KEY: MISC_FEATURE
<222> LOCATION: (10)..(10)
<223> OTHER INFORMATION: Xaa10 can be represented by any amino acid of
      G, A, V, L or I
<220> FEATURE:
<221> NAME/KEY: MISC_FEATURE
<222> LOCATION: (11)..(11)
<223> OTHER INFORMATION: Xaa11 can be represented by any amino acid of
      F, Y or W
<220> FEATURE:
<221> NAME/KEY: MISC_FEATURE
<222> LOCATION: (12)..(12)
<223> OTHER INFORMATION: Xaa12 can be represented by any amino acid of
      F, Y or W
<220> FEATURE:
<221> NAME/KEY: MISC_FEATURE
<222> LOCATION: (13)..(13)
<223> OTHER INFORMATION: Xaa13 can be represented by any amino acid of
      D, E, N or Q
<220> FEATURE:
<221> NAME/KEY: MISC_FEATURE
<222> LOCATION: (14)..(14)
<223> OTHER INFORMATION: Xaa14 can be represented by any amino acid of
      S, G, A, V, L or I
<220> FEATURE:
<221> NAME/KEY: MISC_FEATURE
<222> LOCATION: (15)..(15)
<223> OTHER INFORMATION: Xaa15 can be represented by any amino acid of
      D, E, N or Q
<220> FEATURE:
<221> NAME/KEY: MISC_FEATURE
```

-continued

```
<222> LOCATION: (16)..(16)
<223> OTHER INFORMATION: Xaa16 can be represented by any amino acid of
      P, G, S, A or T
<220> FEATURE:
<221> NAME/KEY: MISC_FEATURE
<222> LOCATION: (17)..(17)
<223> OTHER INFORMATION: Xaa17 can be represented by any amino acid of
      G, A, V, L or I
<220> FEATURE:
<221> NAME/KEY: MISC_FEATURE
<222> LOCATION: (18)..(18)
<223> OTHER INFORMATION: Xaa18 can be represented by any amino acid of
      D, E, N or Q
<220> FEATURE:
<221> NAME/KEY: MISC_FEATURE
<222> LOCATION: (19)..(19)
<223> OTHER INFORMATION: Xaa19 can be represented by any amino acid of
      G, A, V, L or I
<220> FEATURE:
<221> NAME/KEY: MISC_FEATURE
<222> LOCATION: (20)..(20)
<223> OTHER INFORMATION: Xaa20 can be represented by any amino acid of
      G, A, V, L or I
<220> FEATURE:
<221> NAME/KEY: MISC_FEATURE
<222> LOCATION: (21)..(21)
<223> OTHER INFORMATION: Xaa21 can be represented by any amino acid of
      S, C, T or M

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 8
<211> LENGTH: 21
<212> TYPE: PRT
<213> ORGANISM: Artificial Sequence
<220> FEATURE:
<223> OTHER INFORMATION: Sequence is compeletely synthesized
<220> FEATURE:
<221> NAME/KEY: MISC_FEATURE
<222> LOCATION: (1)..(1)
<223> OTHER INFORMATION: Xaa1 can be represented by any amino acid of H,
      K or R
<220> FEATURE:
<221> NAME/KEY: MISC_FEATURE
<222> LOCATION: (2)..(2)
<223> OTHER INFORMATION: Xaa2 can be represented by any amino acid of F,
      Y or W
<220> FEATURE:
<221> NAME/KEY: MISC_FEATURE
<222> LOCATION: (3)..(3)
<223> OTHER INFORMATION: Xaa3 can be represented by any amino acid of D,
      E, N or Q
<220> FEATURE:
<221> NAME/KEY: MISC_FEATURE
<222> LOCATION: (4)..(4)
<223> OTHER INFORMATION: Xaa4 can be represented by any amino acid of G,
      A, V, L or I
<220> FEATURE:
<221> NAME/KEY: MISC_FEATURE
<222> LOCATION: (5)..(5)
<223> OTHER INFORMATION: Xaa5 can be represented by any amino acid of S,
      C, T or M
<220> FEATURE:
<221> NAME/KEY: MISC_FEATURE
<222> LOCATION: (6)..(6)
<223> OTHER INFORMATION: Xaa6 can be represented by any amino acid of G,
      A, V, L or I
<220> FEATURE:
<221> NAME/KEY: MISC_FEATURE
<222> LOCATION: (7)..(7)
<223> OTHER INFORMATION: Xaa7 can be represented by any amino acid of G,
      A, V, L or I
```

-continued

```
<220> FEATURE:
<221> NAME/KEY: MISC_FEATURE
<222> LOCATION: (8)..(8)
<223> OTHER INFORMATION: Xaa8 can be represented by any amino acid of D,
      E, N or Q
<220> FEATURE:
<221> NAME/KEY: MISC_FEATURE
<222> LOCATION: (9)..(9)
<223> OTHER INFORMATION: Xaa9 can be represented by any amino acid of G,
      A, V, L or I
<220> FEATURE:
<221> NAME/KEY: MISC_FEATURE
<222> LOCATION: (10)..(10)
<223> OTHER INFORMATION: Xaa10 can be represented by any amino acid of
      S, C, T or M
<220> FEATURE:
<221> NAME/KEY: MISC_FEATURE
<222> LOCATION: (11)..(11)
<223> OTHER INFORMATION: Xaa11 can be represented by any amino acid of
      G, A, V, L or I
<220> FEATURE:
<221> NAME/KEY: MISC_FEATURE
<222> LOCATION: (12)..(12)
<223> OTHER INFORMATION: Xaa12 can be represented by any amino acid of
      P, G, S, A or T
<220> FEATURE:
<221> NAME/KEY: MISC_FEATURE
<222> LOCATION: (13)..(13)
<223> OTHER INFORMATION: Xaa13 can be represented by any amino acid of
      S, C, T or M
<220> FEATURE:
<221> NAME/KEY: MISC_FEATURE
<222> LOCATION: (14)..(14)
<223> OTHER INFORMATION: Xaa14 can be represented by any amino acid of
      G, A, V, L or I
<220> FEATURE:
<221> NAME/KEY: MISC_FEATURE
<222> LOCATION: (15)..(15)
<223> OTHER INFORMATION: Xaa15 can be represented by any amino acid of
      D, E, N or Q
<220> FEATURE:
<221> NAME/KEY: MISC_FEATURE
<222> LOCATION: (16)..(16)
<223> OTHER INFORMATION: Xaa16 can be represented by any amino acid of
      P, G, S, A or T
<220> FEATURE:
<221> NAME/KEY: MISC_FEATURE
<222> LOCATION: (17)..(17)
<223> OTHER INFORMATION: Xaa17 can be represented by any amino acid of
      G, A, V, L or I
<220> FEATURE:
<221> NAME/KEY: MISC_FEATURE
<222> LOCATION: (18)..(18)
<223> OTHER INFORMATION: Xaa18 can be represented by any amino acid of
      D, E, N or Q
<220> FEATURE:
<221> NAME/KEY: MISC_FEATURE
<222> LOCATION: (19)..(19)
<223> OTHER INFORMATION: Xaa19 can be represented by any amino acid of
      G, A, V, L or I
<220> FEATURE:
<221> NAME/KEY: MISC_FEATURE
<222> LOCATION: (20)..(20)
<223> OTHER INFORMATION: Xaa20 can be represented by any amino acid of
      G, A, V, L or I
<220> FEATURE:
<221> NAME/KEY: MISC_FEATURE
<222> LOCATION: (21)..(21)
<223> OTHER INFORMATION: Xaa21 can be represented by any amino acid of
      S, C, T or M

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
        20
```

-continued

```
<210> SEQ ID NO 9
<211> LENGTH: 9
<212> TYPE: PRT
<213> ORGANISM: Artificial Sequence
<220> FEATURE:
<223> OTHER INFORMATION: Sequence is completely synthesized

<400> SEQUENCE: 9

Met Gly Gln Pro Leu Gln Val Leu Thr
1               5

<210> SEQ ID NO 10
<211> LENGTH: 4
<212> TYPE: PRT
<213> ORGANISM: Artificial Sequence
<220> FEATURE:
<223> OTHER INFORMATION: Sequence is completely synthesized

<400> SEQUENCE: 10

Gln Val Leu Thr
1

<210> SEQ ID NO 11
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 11

Leu Gln Val Leu Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Sequence is completely synthesized

<400> SEQUENCE: 12

Pro Leu Gln Val Leu Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Sequence is completely synthesized

<400> SEQUENCE: 13

Gln Pro Leu Gln Val Leu Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Sequence is completely synthesized

<400> SEQUENCE: 14

Gly Gln Pro Leu Gln Val Leu Thr
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: Sequence is completely synthesized

<400> SEQUENCE: 15

Gln Gly Gln Pro Leu Gln Val Leu Thr
1               5

<210> SEQ ID NO 16
<211> LENGTH: 10
<212> TYPE: PRT
<213> ORGANISM: Artificial Sequence
<220> FEATURE:
<223> OTHER INFORMATION: Sequence is completely synthesized

<400> SEQUENCE: 16

Phe Gln Gly Gln Pro Leu Gln Val Leu Thr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Sequence is completely synthesized

<400> SEQUENCE: 17

Tyr Phe Gln Gly Gln Pro Leu Gln Val Leu Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Sequence is completely synthesized

<400> SEQUENCE: 18

Leu Tyr Phe Gln Gly Gln Pro Leu Gln Val Leu Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Sequence is completely synthesized

<400> SEQUENCE: 19

Asn Leu Tyr Phe Gln Gly Gln Pro Leu Gln Val Leu Thr
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Sequence is completely synthesized

<400> SEQUENCE: 20

Glu Asn Leu Tyr Phe Gln Gly Gln Pro Leu Gln Val Leu Thr
1               5                   10

<210> SEQ ID NO 21
```

```
<211> LENGTH: 15
<212> TYPE: PRT
<213> ORGANISM: Artificial Sequence
<220> FEATURE:
<223> OTHER INFORMATION: Sequence is completely synthesized

<400> SEQUENCE: 21

Ser Glu Asn Leu Tyr Phe Gln Gly Gln Pro Leu Gln Val Leu Thr
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Sequence is completely synthesized

<400> SEQUENCE: 22

Gly Ser Glu Asn Leu Tyr Phe Gln Gly Gln Pro Leu Gln Val Leu Thr
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: Sequence is completely synthesized

<400> SEQUENCE: 23

Thr Gly Ser Glu Asn Leu Tyr Phe Gln Gly Gln Pro Leu Gln Val Leu
1               5                   10                  15

Thr

<210> SEQ ID NO 24
<211> LENGTH: 18
<212> TYPE: PRT
<213> ORGANISM: Artificial Sequence
<220> FEATURE:
<223> OTHER INFORMATION: Sequence is completely synthesized

<400> SEQUENCE: 24

Gly Thr Gly Ser Glu Asn Leu Tyr Phe Gln Gly Gln Pro Leu Gln Val
1               5                   10                  15

Leu Thr

<210> SEQ ID NO 25
<211> LENGTH: 19
<212> TYPE: PRT
<213> ORGANISM: Artificial Sequence
<220> FEATURE:
<223> OTHER INFORMATION: Sequence is completely synthesized

<400> SEQUENCE: 25

Leu Gly Thr Gly Ser Glu Asn Leu Tyr Phe Gln Gly Gln Pro Leu Gln
1               5                   10                  15

Val Leu Thr

<210> SEQ ID NO 26
<211> LENGTH: 20
<212> TYPE: PRT
<213> ORGANISM: Artificial Sequence
<220> FEATURE:
<223> OTHER INFORMATION: Sequence is completely synthesized

<400> SEQUENCE: 26
```

-continued

```
Asp Leu Gly Thr Gly Ser Glu Asn Leu Tyr Phe Gln Gly Gln Pro Leu
1               5                   10                  15

Gln Val Leu Thr
            20

<210> SEQ ID NO 27
<211> LENGTH: 11
<212> TYPE: PRT
<213> ORGANISM: Artificial Sequence
<220> FEATURE:
<223> OTHER INFORMATION: Sequence is completely synthesized

<400> SEQUENCE: 27

Gly Pro Met Gly Gln Pro Leu Gln Val Leu Thr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Sequence is completely synthesized

<400> SEQUENCE: 28

Met Gly Pro Met Gly Gln Pro Leu Gln Val Leu Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Sequence is completely synthesized

<400> SEQUENCE: 29

Val Met Gly Pro Met Gly Gln Pro Leu Gln Val Leu Thr
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Sequence is completely synthesized

<400> SEQUENCE: 30

Gln Val Met Gly Pro Met Gly Gln Pro Leu Gln Val Leu Thr
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Sequence is completely synthesized

<400> SEQUENCE: 31

Ala Gln Val Met Gly Pro Met Gly Gln Pro Leu Gln Val Leu Thr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Sequence is completely synthesized
```

-continued

```
<400> SEQUENCE: 32

Gly Ala Gln Val Met Gly Pro Met Gly Gln Pro Leu Gln Val Leu Thr
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Sequence is completely synthesized

<400> SEQUENCE: 33

Ser Gly Ala Gln Val Met Gly Pro Met Gly Gln Pro Leu Gln Val Leu
1               5                   10                  15

Thr

<210> SEQ ID NO 34
<211> LENGTH: 18
<212> TYPE: PRT
<213> ORGANISM: Artificial Sequence
<220> FEATURE:
<223> OTHER INFORMATION: Sequence is completely synthesized

<400> SEQUENCE: 34

Gly Ser Gly Ala Gln Val Met Gly Pro Met Gly Gln Pro Leu Gln Val
1               5                   10                  15

Leu Thr

<210> SEQ ID NO 35
<211> LENGTH: 19
<212> TYPE: PRT
<213> ORGANISM: Artificial Sequence
<220> FEATURE:
<223> OTHER INFORMATION: Sequence is completely synthesized

<400> SEQUENCE: 35

Glu Gly Ser Gly Ala Gln Val Met Gly Pro Met Gly Gln Pro Leu Gln
1               5                   10                  15

Val Leu Thr

<210> SEQ ID NO 36
<211> LENGTH: 20
<212> TYPE: PRT
<213> ORGANISM: Artificial Sequence
<220> FEATURE:
<223> OTHER INFORMATION: Sequence is completely synthesized

<400> SEQUENCE: 36

Phe Glu Gly Ser Gly Ala Gln Val Met Gly Pro Met Gly Gln Pro Leu
1               5                   10                  15

Gln Val Leu Thr
            20

<210> SEQ ID NO 37
<211> LENGTH: 10
<212> TYPE: PRT
<213> ORGANISM: Artificial Sequence
<220> FEATURE:
<223> OTHER INFORMATION: Sequence is completely synthesized

<400> SEQUENCE: 37

Pro Met Gly Gln Pro Leu Gln Val Leu Thr
1               5                   10
```

```
<210> SEQ ID NO 38
<211> LENGTH: 8
<212> TYPE: PRT
<213> ORGANISM: Artificial Sequence
<220> FEATURE:
<223> OTHER INFORMATION: Sequence is completely synthesized

<400> SEQUENCE: 38

His His His His His His His His
1               5

<210> SEQ ID NO 39
<211> LENGTH: 7
<212> TYPE: PRT
<213> ORGANISM: Artificial Sequence
<220> FEATURE:
<223> OTHER INFORMATION: Sequence is completely synthesized
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa7 is G or S

<400> SEQUENCE: 39

Glu Xaa Xaa Tyr Xaa Gln Xaa
1               5

<210> SEQ ID NO 40
<211> LENGTH: 7
<212> TYPE: PRT
<213> ORGANISM: Artificial Sequence
<220> FEATURE:
<223> OTHER INFORMATION: Sequence is completely synthesized

<400> SEQUENCE: 40

Glu Asn Leu Tyr Phe Gln Gly
1               5

<210> SEQ ID NO 41
<211> LENGTH: 17
<212> TYPE: PRT
<213> ORGANISM: Artificial Sequence
<220> FEATURE:
<223> OTHER INFORMATION: Sequence is completely synthesized

<400> SEQUENCE: 41

Val Ser Gln Thr Ser Lys Leu Thr Arg Ala Glu Thr Val Phe Pro Asp
1               5                   10                  15

Val

<210> SEQ ID NO 42
<211> LENGTH: 6
<212> TYPE: PRT
<213> ORGANISM: Artificial Sequence
<220> FEATURE:
<223> OTHER INFORMATION: Sequence is completely synthesized

<400> SEQUENCE: 42

Pro Leu Gly Leu Trp Ala
1               5
```

-continued

```
<210> SEQ ID NO 43
<211> LENGTH: 6
<212> TYPE: PRT
<213> ORGANISM: Artificial Sequence
<220> FEATURE:
<223> OTHER INFORMATION: Sequence is completely synthesized

<400> SEQUENCE: 43

Arg Val Leu Ala Glu Ala
1               5

<210> SEQ ID NO 44
<211> LENGTH: 10
<212> TYPE: PRT
<213> ORGANISM: Artificial Sequence
<220> FEATURE:
<223> OTHER INFORMATION: Sequence is completely synthesized

<400> SEQUENCE: 44

Glu Asp Val Val Cys Cys Ser Met Ser Tyr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Sequence is completely synthesized

<400> SEQUENCE: 45

Gly Gly Ile Glu Gly Arg Gly Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Sequence is completely synthesized

<400> SEQUENCE: 46

Thr Arg His Arg Gln Pro Arg Gly Trp Glu
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Sequence is completely synthesized

<400> SEQUENCE: 47

Ala Gly Asn Arg Val Arg Arg Ser Val Gly
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Sequence is completely synthesized

<400> SEQUENCE: 48

Arg Arg Arg Arg Arg Arg Arg Arg Arg
1               5
```

-continued

```
<210> SEQ ID NO 49
<211> LENGTH: 4
<212> TYPE: PRT
<213> ORGANISM: Artificial Sequence
<220> FEATURE:
<223> OTHER INFORMATION: Sequence is completely synthesized

<400> SEQUENCE: 49

Gly Phe Leu Gly
1

<210> SEQ ID NO 50
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 50

Asp Asp Asp Asp Lys
1               5

<210> SEQ ID NO 51
<211> LENGTH: 6
<212> TYPE: PRT
<213> ORGANISM: Artificial Sequence
<220> FEATURE:
<223> OTHER INFORMATION: Sequence is completely synthesized

<400> SEQUENCE: 51

Leu Val Pro Arg Gly Ser
1               5

<210> SEQ ID NO 52
<211> LENGTH: 8
<212> TYPE: PRT
<213> ORGANISM: Artificial Sequence
<220> FEATURE:
<223> OTHER INFORMATION: Sequence is completely synthesized

<400> SEQUENCE: 52

Leu Glu Val Leu Phe Gln Gly Pro
1               5

<210> SEQ ID NO 53
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 53

Asp Asp Asp Asp Lys
1               5

<210> SEQ ID NO 54
<211> LENGTH: 6
<212> TYPE: PRT
<213> ORGANISM: Artificial Sequence
<220> FEATURE:
<223> OTHER INFORMATION: Sequence is completely synthesized

<400> SEQUENCE: 54

Leu Val Pro Arg Gly Ser
1               5

<210> SEQ ID NO 55
```

```
<211> LENGTH: 30
<212> TYPE: PRT
<213> ORGANISM: Artificial Sequence
<220> FEATURE:
<223> OTHER INFORMATION: Sequence is completely synthesized

<400> SEQUENCE: 55

Ser Ser Gly Leu Val Pro Arg Gly Ser His Met Ala Ser Met Thr Gly
1               5                   10                  15

Gly Gln Gln Met Gly Arg Gly Ser Asp Asp Asp Asp Lys Met
            20                  25                  30

<210> SEQ ID NO 56
<211> LENGTH: 4
<212> TYPE: PRT
<213> ORGANISM: Artificial Sequence
<220> FEATURE:
<223> OTHER INFORMATION: Sequence is completely synthesized

<400> SEQUENCE: 56

Gly Gly Gly Ser
1

<210> SEQ ID NO 57
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 57

Gly Gly Gly Gly Ser
1               5

<210> SEQ ID NO 58
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 58

Ala Arg Thr Ile Asn
1               5

<210> SEQ ID NO 59
<211> LENGTH: 4
<212> TYPE: PRT
<213> ORGANISM: Artificial Sequence
<220> FEATURE:
<223> OTHER INFORMATION: Sequence is completely synthesized

<400> SEQUENCE: 59

Glu Glu Glu Lys
1

<210> SEQ ID NO 60
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 60

Glu Ala Ala Ala Lys
1               5
```

<210> SEQ ID NO 61
<211> LENGTH: 16
<212> TYPE: PRT
<213> ORGANISM: Artificial Sequence
<220> FEATURE:
<223> OTHER INFORMATION: Sequence is completely synthesized

<400> SEQUENCE: 61

Ala Glu Ala Ala Ala Lys Ala Leu Glu Ala Glu Ala Ala Ala Lys Ala
1               5                   10                  15

<210> SEQ ID NO 62
<211> LENGTH: 5
<212> TYPE: PRT
<213> ORGANISM: Artificial Sequence
<220> FEATURE:
<223> OTHER INFORMATION: Sequence is completely synthesized

<400> SEQUENCE: 62

Pro Ala Pro Ala Pro
1               5

<210> SEQ ID NO 63
<211> LENGTH: 7
<212> TYPE: PRT
<213> ORGANISM: Artificial Sequence
<220> FEATURE:
<223> OTHER INFORMATION: Sequence is completely synthesized

<400> SEQUENCE: 63

Pro Asp Leu Gly Thr Gly Ser
1               5

<210> SEQ ID NO 64
<211> LENGTH: 23
<212> TYPE: PRT
<213> ORGANISM: Artificial Sequence
<220> FEATURE:
<223> OTHER INFORMATION: Sequence is completely synthesized

<400> SEQUENCE: 64

Met Gly His His His His His His His His Pro Asp Leu Gly Thr Gly
1               5                   10                  15

Ser Glu Asn Leu Tyr Phe Gln
            20

<210> SEQ ID NO 65
<211> LENGTH: 24
<212> TYPE: PRT
<213> ORGANISM: Artificial Sequence
<220> FEATURE:
<223> OTHER INFORMATION: Sequence is completely synthesized

<400> SEQUENCE: 65

Met Gly His His His His His His His His Pro Asp Leu Gly Thr Gly
1               5                   10                  15

Ser Glu Asn Leu Tyr Phe Gln Gly
            20

<210> SEQ ID NO 66
<211> LENGTH: 24
<212> TYPE: PRT
<213> ORGANISM: Artificial Sequence
<220> FEATURE:
<223> OTHER INFORMATION: Sequence is completely synthesized

<400> SEQUENCE: 66

Met Gly His His His His His His His Pro Asp Leu Gly Thr Gly
1               5                   10                  15

Ser Glu Asn Leu Tyr Phe Gln Ser
            20

<210> SEQ ID NO 67
<211> LENGTH: 663
<212> TYPE: PRT
<213> ORGANISM: Artificial Sequence
<220> FEATURE:
<223> OTHER INFORMATION: Sequence is completely syntesized

<400> SEQUENCE: 67

Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
            20                  25                  30

Ala Glu Thr Gly Gly Met Gly Leu Ala Val Arg Gln Ala Pro Leu Ile
            35                  40                  45

Ile Pro Leu Lys Ala Thr Ser Thr Pro Val Ser Ile Lys Gln Tyr Pro
        50                  55                  60

Met Ser Gln Lys Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
                100                 105                 110

Asp Leu Arg Glu Val Asn Lys Arg Val Glu Asp Ile His Pro Thr Val
            115                 120                 125

Pro Asn Pro Tyr Asn Leu Leu Ser Gly Leu Pro Pro Ser His Gln Trp
        130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
                180                 185                 190

Asn Ser Pro Thr Leu Phe Asp Glu Ala Leu His Arg Asp Leu Ala Asp
            195                 200                 205

Phe Arg Ile Gln His Pro Asp Leu Ile Leu Leu Gln Tyr Val Asp Asp
        210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
                260                 265                 270

Lys Glu Gly Gln Arg Trp Leu Thr Glu Ala Arg Lys Glu Thr Val Met
            275                 280                 285

Gly Gln Pro Thr Pro Lys Thr Pro Arg Gln Leu Arg Arg Phe Leu Gly
        290                 295                 300

Thr Ala Gly Phe Cys Arg Leu Phe Ile Pro Gly Phe Ala Glu Met Ala
305                 310                 315                 320

Ala Pro Leu Tyr Pro Leu Thr Lys Thr Gly Thr Leu Phe Asn Trp Gly

```
                325                 330                 335

Pro Asp Gln Gln Lys Ala Tyr Gln Glu Ile Lys Gln Ala Leu Leu Thr
            340                 345                 350

Ala Pro Ala Leu Gly Leu Pro Asp Leu Thr Lys Pro Phe Glu Leu Phe
            355                 360                 365

Val Asp Glu Lys Gln Gly Tyr Ala Lys Gly Val Leu Thr Gln Lys Leu
        370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
            420                 425                 430

Ile Gly Ala Pro His Ala Val Glu Ala Leu Val Lys Gln Pro Pro Asp
            435                 440                 445

Arg Trp Leu Ser Lys Ala Arg Met Thr His Tyr Gln Ala Leu Leu Leu
        450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
                485                 490                 495

Ile Leu Ala Glu Ala His Gly Thr Arg Pro Asp Leu Thr Asp Gln Pro
            500                 505                 510

Leu Pro Asp Ala Asp His Thr Trp Tyr Thr Asn Gly Ser Ser Leu Leu
            515                 520                 525

Gln Glu Gly Gln Arg Lys Ala Gly Ala Ala Val Thr Thr Glu Thr Glu
        530                 535                 540

Val Ile Trp Ala Lys Ala Leu Pro Ala Gly Thr Ser Ala Gln Arg Ala
545                 550                 555                 560

Glu Leu Ile Ala Leu Thr Gln Ala Leu Lys Met Ala Glu Gly Lys Lys
                565                 570                 575

Leu Asn Val Tyr Thr Asp Ser Arg Tyr Ala Phe Ala Thr Ala His Ile
            580                 585                 590

His Gly Glu Ile Tyr Arg Arg Arg Gly Leu Leu Thr Ser Glu Gly Lys
            595                 600                 605

Glu Ile Lys Asn Lys Asp Glu Ile Leu Ala Leu Leu Lys Ala Leu Phe
        610                 615                 620

Leu Pro Lys Arg Leu Ser Ile Ile His Cys Pro Gly His Gln Lys Gly
625                 630                 635                 640

His Ser Ala Glu Ala Arg Gly Asn Arg Met Ala Asp Gln Ala Ala Arg
                645                 650                 655

Lys Ala Ala Ile Thr Glu Thr
            660

<210> SEQ ID NO 68
<211> LENGTH: 671
<212> TYPE: PRT
<213> ORGANISM: Artificial Sequence
<220> FEATURE:
<223> OTHER INFORMATION: Sequence is completely syntesized

<400> SEQUENCE: 68

Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
```

-continued

```
               20                  25                  30
Ala Glu Thr Gly Gly Met Gly Leu Ala Val Arg Gln Ala Pro Leu Ile
        35                  40                  45

Ile Pro Leu Lys Ala Thr Ser Thr Pro Val Ser Ile Lys Gln Tyr Pro
    50                  55                  60

Met Ser Gln Lys Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Gly Leu Pro Pro Ser His Gln Trp
    130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Ala Asp
        195                 200                 205

Phe Arg Ile Gln His Pro Asp Leu Ile Leu Leu Gln Tyr Val Asp Asp
    210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
            260                 265                 270

Lys Glu Gly Gln Arg Trp Leu Thr Glu Ala Arg Lys Glu Thr Val Met
        275                 280                 285

Gly Gln Pro Thr Pro Lys Thr Pro Arg Gln Leu Arg Arg Phe Leu Gly
    290                 295                 300

Thr Ala Gly Phe Cys Arg Leu Phe Ile Pro Gly Phe Ala Glu Met Ala
305                 310                 315                 320

Ala Pro Leu Tyr Pro Leu Thr Lys Thr Gly Thr Leu Phe Asn Trp Gly
                325                 330                 335

Pro Asp Gln Gln Lys Ala Tyr Gln Glu Ile Lys Gln Ala Leu Leu Thr
            340                 345                 350

Ala Pro Ala Leu Gly Leu Pro Asp Leu Thr Lys Pro Phe Glu Leu Phe
        355                 360                 365

Val Asp Glu Lys Gln Gly Tyr Ala Lys Gly Val Leu Thr Gln Lys Leu
    370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
            420                 425                 430

Ile Gly Ala Pro His Ala Val Glu Ala Leu Val Lys Gln Pro Pro Asp
        435                 440                 445
```

-continued

```
Arg Trp Leu Ser Lys Ala Arg Met Thr His Tyr Gln Ala Leu Leu Leu
    450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
                485                 490                 495

Ile Leu Ala Glu Ala His Gly Thr Arg Pro Asp Leu Thr Asp Gln Pro
                500                 505                 510

Leu Pro Asp Ala Asp His Thr Trp Tyr Thr Asn Gly Ser Ser Leu Leu
                515                 520                 525

Gln Glu Gly Gln Arg Lys Ala Gly Ala Ala Val Thr Thr Glu Thr Glu
    530                 535                 540

Val Ile Trp Ala Lys Ala Leu Pro Ala Gly Thr Ser Ala Gln Arg Ala
545                 550                 555                 560

Glu Leu Ile Ala Leu Thr Gln Ala Leu Lys Met Ala Glu Gly Lys Lys
                565                 570                 575

Leu Asn Val Tyr Thr Asp Ser Arg Tyr Ala Phe Ala Thr Ala His Ile
                580                 585                 590

His Gly Glu Ile Tyr Arg Arg Arg Gly Leu Leu Thr Ser Glu Gly Lys
    595                 600                 605

Glu Ile Lys Asn Lys Asp Glu Ile Leu Ala Leu Leu Lys Ala Leu Phe
    610                 615                 620

Leu Pro Lys Arg Leu Ser Ile Ile His Cys Pro Gly His Gln Lys Gly
625                 630                 635                 640

His Ser Ala Glu Ala Arg Gly Asn Arg Met Ala Asp Gln Ala Ala Arg
                645                 650                 655

Lys Ala Ala Ile Thr Glu Thr Pro Asp Thr Ser Thr Leu Leu Ile
                660                 665                 670
```

```
<210> SEQ ID NO 69
<211> LENGTH: 791
<212> TYPE: PRT
<213> ORGANISM: Artificial Sequence
<220> FEATURE:
<223> OTHER INFORMATION: Sequence is completely synthesized

<400> SEQUENCE: 69
```

```
Met Ser Asp Lys Ile Ile His Leu Thr Asp Asp Ser Phe Asp Thr Asp
1               5                   10                  15

Val Leu Lys Ala Asp Gly Ala Ile Leu Val Ala Phe Trp Ala His Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp His Asn
    50                  55                  60

Pro Gly Thr Ala Pro Lys Tyr Gly Ile Arg Ser Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly Glu Asn Leu Tyr Phe Gln Gly Gln Pro Leu Gln Val Leu Thr
        115                 120                 125

Leu Asn Ile Glu Asp Glu His Arg Leu His Glu Thr Ser Lys Glu Pro
    130                 135                 140
```

```
Asp Val Ser Leu Gly Ser Thr Trp Leu Ser Asp Phe Pro Gln Ala Trp
145                 150                 155                 160

Ala Glu Thr Gly Gly Met Gly Leu Ala Val Arg Gln Ala Pro Leu Ile
                165                 170                 175

Ile Pro Leu Lys Ala Thr Ser Thr Pro Val Ser Ile Lys Gln Tyr Pro
                180                 185                 190

Met Ser Gln Lys Ala Arg Leu Gly Ile Lys Pro His Ile Gln Arg Leu
                195                 200                 205

Leu Asp Gln Gly Ile Leu Val Pro Cys Gln Ser Pro Trp Asn Thr Pro
                210                 215                 220

Leu Leu Pro Val Lys Lys Pro Gly Thr Asn Asp Tyr Arg Pro Val Gln
225                 230                 235                 240

Asp Leu Arg Glu Val Asn Lys Arg Val Glu Asp Ile His Pro Thr Val
                245                 250                 255

Pro Asn Pro Tyr Asn Leu Leu Ser Gly Leu Pro Pro Ser His Gln Trp
                260                 265                 270

Tyr Thr Val Leu Asp Leu Lys Asp Ala Phe Phe Cys Leu Arg Leu His
                275                 280                 285

Pro Thr Ser Gln Pro Leu Phe Ala Phe Glu Trp Arg Asp Pro Glu Met
                290                 295                 300

Gly Ile Ser Gly Gln Leu Thr Trp Thr Arg Leu Pro Gln Gly Phe Lys
305                 310                 315                 320

Asn Ser Pro Thr Leu Phe Asp Glu Ala Leu His Arg Asp Leu Ala Asp
                325                 330                 335

Phe Arg Ile Gln His Pro Asp Leu Ile Leu Leu Gln Tyr Val Asp Asp
                340                 345                 350

Leu Leu Leu Ala Ala Thr Ser Glu Leu Asp Cys Gln Gln Gly Thr Arg
                355                 360                 365

Ala Leu Leu Gln Thr Leu Gly Asn Leu Gly Tyr Arg Ala Ser Ala Lys
                370                 375                 380

Lys Ala Gln Ile Cys Gln Lys Gln Val Lys Tyr Leu Gly Tyr Leu Leu
385                 390                 395                 400

Lys Glu Gly Gln Arg Trp Leu Thr Glu Ala Arg Lys Glu Thr Val Met
                405                 410                 415

Gly Gln Pro Thr Pro Lys Thr Pro Arg Gln Leu Arg Arg Phe Leu Gly
                420                 425                 430

Thr Ala Gly Phe Cys Arg Leu Phe Ile Pro Gly Phe Ala Glu Met Ala
                435                 440                 445

Ala Pro Leu Tyr Pro Leu Thr Lys Thr Gly Thr Leu Phe Asn Trp Gly
                450                 455                 460

Pro Asp Gln Gln Lys Ala Tyr Gln Glu Ile Lys Gln Ala Leu Leu Thr
465                 470                 475                 480

Ala Pro Ala Leu Gly Leu Pro Asp Leu Thr Lys Pro Phe Glu Leu Phe
                485                 490                 495

Val Asp Glu Lys Gln Gly Tyr Ala Lys Gly Val Leu Thr Gln Lys Leu
                500                 505                 510

Gly Pro Trp Arg Arg Pro Val Ala Tyr Leu Ser Lys Lys Leu Asp Pro
                515                 520                 525

Val Ala Ala Gly Trp Pro Pro Cys Leu Arg Met Val Ala Ala Ile Ala
                530                 535                 540

Val Leu Thr Lys Asp Ala Gly Lys Leu Thr Met Gly Gln Pro Leu Val
545                 550                 555                 560
```

-continued

```
Ile Gly Ala Pro His Ala Val Glu Ala Leu Val Lys Gln Pro Pro Asp
            565             570             575

Arg Trp Leu Ser Lys Ala Arg Met Thr His Tyr Gln Ala Leu Leu Leu
            580             585             590

Asp Thr Asp Arg Val Gln Phe Gly Pro Val Val Ala Leu Asn Pro Ala
            595             600             605

Thr Leu Leu Pro Leu Pro Glu Glu Gly Leu Gln His Asn Cys Leu Asp
        610             615             620

Ile Leu Ala Glu Ala His Gly Thr Arg Pro Asp Leu Thr Asp Gln Pro
625             630             635             640

Leu Pro Asp Ala Asp His Thr Trp Tyr Thr Asn Gly Ser Ser Leu Leu
            645             650             655

Gln Glu Gly Gln Arg Lys Ala Gly Ala Ala Val Thr Thr Glu Thr Glu
            660             665             670

Val Ile Trp Ala Lys Ala Leu Pro Ala Gly Thr Ser Ala Gln Arg Ala
            675             680             685

Glu Leu Ile Ala Leu Thr Gln Ala Leu Lys Met Ala Glu Gly Lys Lys
            690             695             700

Leu Asn Val Tyr Thr Asp Ser Arg Tyr Ala Phe Ala Thr Ala His Ile
705             710             715             720

His Gly Glu Ile Tyr Arg Arg Arg Gly Leu Leu Thr Ser Glu Gly Lys
            725             730             735

Glu Ile Lys Asn Lys Asp Glu Ile Leu Ala Leu Leu Lys Ala Leu Phe
            740             745             750

Leu Pro Lys Arg Leu Ser Ile Ile His Cys Pro Gly His Gln Lys Gly
            755             760             765

His Ser Ala Glu Ala Arg Gly Asn Arg Met Ala Asp Gln Ala Ala Arg
        770             775             780

Lys Ala Ala Ile Thr Glu Thr
785             790
```

```
<210> SEQ ID NO 70
<211> LENGTH: 716
<212> TYPE: PRT
<213> ORGANISM: Artificial Sequence
<220> FEATURE:
<223> OTHER INFORMATION: Sequence is completely synthesized

<400> SEQUENCE: 70
```

```
Met Gly Gly Ser His His His His His His Gly Met Ala Ser Met Thr
1               5               10              15

Gly Gly Gln Gln Met Gly Arg Asp Leu Tyr Asp Asp Asp Lys His
            20              25              30

Met Thr Leu Asn Ile Glu Asp Glu Tyr Arg Leu His Glu Thr Ser Lys
        35              40              45

Glu Pro Asp Val Ser Leu Gly Ser Thr Trp Leu Ser Asp Phe Pro Gln
        50              55              60

Ala Trp Ala Glu Thr Gly Gly Met Gly Leu Ala Val Arg Gln Ala Pro
65              70              75              80

Leu Ile Ile Leu Leu Lys Ala Thr Ser Thr Pro Val Ser Ile Lys Gln
            85              90              95

Tyr Pro Met Ser Gln Glu Ala Arg Leu Gly Ile Lys Pro His Ile Gln
            100             105             110

Arg Leu Leu Asp Gln Gly Ile Leu Val Pro Cys Gln Ser Pro Trp Asn
            115             120             125
```

```
Thr Pro Leu Leu Pro Val Lys Lys Pro Gly Thr Asn Asp Tyr Arg Pro
    130             135             140
```

```
Val Gln Asp Leu Arg Glu Val Asn Lys Arg Val Glu Asp Ile His Pro
145             150             155             160
```

```
Thr Val Pro Asn Pro Tyr Asn Leu Leu Ser Gly Leu Pro Pro Ser His
            165             170             175
```

```
Gln Trp Tyr Thr Val Leu Asp Leu Lys Asp Ala Phe Phe Cys Leu Arg
        180             185             190
```

```
Leu His Pro Thr Ser Gln Pro Leu Phe Ala Phe Glu Trp Arg Asp Pro
        195             200             205
```

```
Glu Met Gly Ile Ser Gly Gln Leu Thr Trp Thr Arg Leu Pro Gln Gly
    210             215             220
```

```
Phe Lys Asn Ser Pro Thr Leu Phe Asp Glu Ala Leu Arg Arg Asp Leu
225             230             235             240
```

```
Ala Asp Phe Arg Ile Gln His Pro Asp Leu Ile Leu Leu Gln Tyr Val
            245             250             255
```

```
Asp Asp Leu Leu Leu Ala Ala Thr Ser Glu Leu Asp Cys Gln Gln Gly
            260             265             270
```

```
Thr Arg Ala Leu Leu Gln Thr Leu Gly Asp Leu Gly Tyr Arg Ala Ser
        275             280             285
```

```
Ala Lys Lys Ala Gln Ile Cys Gln Lys Gln Val Lys Tyr Leu Gly Tyr
    290             295             300
```

```
Leu Leu Lys Glu Gly Gln Arg Trp Leu Thr Glu Ala Arg Lys Glu Thr
305             310             315             320
```

```
Val Met Gly Gln Pro Thr Pro Lys Thr Pro Arg Gln Leu Arg Glu Phe
            325             330             335
```

```
Leu Gly Thr Ala Gly Phe Cys Arg Leu Trp Ile Pro Gly Phe Ala Glu
        340             345             350
```

```
Met Ala Ala Pro Leu Tyr Pro Leu Thr Lys Thr Gly Thr Leu Phe Asn
        355             360             365
```

```
Trp Gly Pro Asp Gln Gln Lys Ala Tyr Gln Glu Ile Lys Gln Ala Leu
    370             375             380
```

```
Leu Thr Ala Pro Ala Leu Gly Leu Pro Asp Leu Thr Lys Pro Phe Glu
385             390             395             400
```

```
Leu Phe Val Asp Glu Lys Gln Gly Tyr Ala Lys Gly Val Leu Thr Gln
            405             410             415
```

```
Lys Leu Gly Pro Trp Arg Arg Pro Val Ala Tyr Leu Ser Lys Lys Leu
        420             425             430
```

```
Asp Pro Val Ala Ala Gly Trp Pro Pro Cys Leu Arg Met Val Ala Ala
        435             440             445
```

```
Ile Ala Val Leu Thr Lys Asp Ala Gly Lys Leu Thr Met Gly Gln Pro
    450             455             460
```

```
Leu Val Ile Leu Ala Pro His Ala Val Glu Ala Leu Val Lys Gln Pro
465             470             475             480
```

```
Pro Asp Arg Trp Leu Ser Asn Ala Arg Met Thr His Tyr Gln Ala Leu
            485             490             495
```

```
Leu Leu Asp Thr Asp Arg Val Gln Phe Gly Pro Val Val Ala Leu Asn
        500             505             510
```

```
Pro Ala Thr Leu Leu Pro Leu Pro Glu Glu Gly Leu Gln His Asn Cys
        515             520             525
```

```
Leu Asp Ile Leu Ala Glu Ala His Gly Thr Arg Pro Asp Leu Thr Asp
    530             535             540
```

```
Gln Pro Leu Pro Asp Ala Asp His Thr Trp Tyr Thr Gly Gly Ser Ser
```

-continued

```
545              550              555              560

Leu Leu Gln Glu Gly Gln Arg Lys Ala Gly Ala Ala Val Thr Thr Glu
             565              570              575

Thr Glu Val Ile Trp Ala Lys Ala Leu Pro Ala Gly Thr Ser Ala Gln
             580              585              590

Arg Ala Gln Leu Ile Ala Leu Thr Gln Ala Leu Arg Met Ala Glu Gly
             595              600              605

Lys Lys Leu Asn Val Tyr Thr Asn Ser Arg Tyr Ala Phe Ala Thr Ala
             610              615              620

His Ile His Gly Glu Ile Tyr Arg Arg Arg Gly Leu Leu Thr Ser Glu
625              630              635              640

Gly Lys Glu Ile Lys Asn Lys Asp Glu Ile Leu Ala Leu Leu Lys Ala
             645              650              655

Leu Phe Leu Pro Lys Arg Leu Ser Ile Ile His Cys Pro Gly His Gln
             660              665              670

Lys Gly His Ser Ala Glu Ala Arg Gly Asn Arg Met Ala Asp Gln Ala
             675              680              685

Ala Arg Lys Ala Ala Ile Thr Glu Asn Pro Asp Thr Ser Thr Leu Leu
             690              695              700

Ile Glu Asn Ser Ser Pro Asn Ser Arg Leu Ile Asn
705              710              715

<210> SEQ ID NO 71
<211> LENGTH: 694
<212> TYPE: PRT
<213> ORGANISM: Artificial Sequence
<220> FEATURE:
<223> OTHER INFORMATION: Sequence is completely synthesized

<400> SEQUENCE: 71

Met Gly His His His His His His His His Pro Asp Leu Gly Thr Gly
1               5               10              15

Ser Glu Asn Leu Tyr Phe Gln Gly Gln Pro Leu Gln Val Leu Thr Leu
             20              25              30

Asn Ile Glu Asp Glu Tyr Arg Leu His Glu Thr Ser Lys Glu Pro Asp
        35              40              45

Val Ser Leu Gly Ser Thr Trp Leu Ser Asp Phe Pro Gln Ala Trp Ala
        50              55              60

Glu Thr Gly Gly Met Gly Leu Ala Val Arg Gln Ala Pro Leu Ile Ile
65              70              75              80

Leu Leu Lys Ala Thr Ser Thr Pro Val Ser Ile Lys Gln Tyr Pro Met
             85              90              95

Ser Gln Glu Ala Arg Leu Gly Ile Lys Pro His Ile Gln Arg Leu Leu
             100             105             110

Asp Gln Gly Ile Leu Val Pro Cys Gln Ser Pro Trp Asn Thr Pro Leu
             115             120             125

Leu Pro Val Lys Lys Pro Gly Thr Asn Asp Tyr Arg Pro Val Gln Asp
        130             135             140

Leu Arg Glu Val Asn Lys Arg Val Glu Asp Ile His Pro Thr Val Pro
145             150             155             160

Asn Pro Tyr Asn Leu Leu Ser Gly Leu Pro Pro Ser His Gln Trp Tyr
             165             170             175

Thr Val Leu Asp Leu Lys Asp Ala Phe Phe Cys Leu Arg Leu His Pro
             180             185             190

Thr Ser Gln Pro Leu Phe Ala Phe Glu Trp Arg Asp Pro Glu Met Gly
```

-continued

```
                   195                200                205

Ile Ser Gly Gln Leu Thr Trp Thr Arg Leu Pro Gln Gly Phe Lys Asn
    210                215                220

Ser Pro Thr Leu Phe Asp Glu Ala Leu Arg Arg Asp Leu Ala Asp Phe
225                230                235                240

Arg Ile Gln His Pro Asp Leu Ile Leu Leu Gln Tyr Val Asp Asp Leu
                   245                250                255

Leu Leu Ala Ala Thr Ser Glu Leu Asp Cys Gln Gln Gly Thr Arg Ala
                   260                265                270

Leu Leu Gln Thr Leu Gly Asp Leu Gly Tyr Arg Ala Ser Ala Lys Lys
                   275                280                285

Ala Gln Ile Cys Gln Lys Gln Val Lys Tyr Leu Gly Tyr Leu Leu Lys
                   290                295                300

Glu Gly Gln Arg Trp Leu Thr Glu Ala Arg Lys Glu Thr Val Met Gly
305                310                315                320

Gln Pro Thr Pro Lys Thr Pro Arg Gln Leu Arg Glu Phe Leu Gly Thr
                   325                330                335

Ala Gly Phe Cys Arg Leu Trp Ile Pro Gly Phe Ala Glu Met Ala Ala
                   340                345                350

Pro Leu Tyr Pro Leu Thr Lys Thr Gly Thr Leu Phe Asn Trp Gly Pro
                   355                360                365

Asp Gln Gln Lys Ala Tyr Gln Glu Ile Lys Gln Ala Leu Leu Thr Ala
                   370                375                380

Pro Ala Leu Gly Leu Pro Asp Leu Thr Lys Pro Phe Glu Leu Phe Val
385                390                395                400

Asp Glu Lys Gln Gly Tyr Ala Lys Gly Val Leu Thr Gln Lys Leu Gly
                   405                410                415

Pro Trp Arg Arg Pro Val Ala Tyr Leu Ser Lys Lys Leu Asp Pro Val
                   420                425                430

Ala Ala Gly Trp Pro Pro Cys Leu Arg Met Val Ala Ala Ile Ala Val
                   435                440                445

Leu Thr Lys Asp Ala Gly Lys Leu Thr Met Gly Gln Pro Leu Val Ile
    450                455                460

Leu Ala Pro His Ala Val Glu Ala Leu Val Lys Gln Pro Pro Asp Arg
465                470                475                480

Trp Leu Ser Asn Ala Arg Met Thr His Tyr Gln Ala Leu Leu Leu Asp
                   485                490                495

Thr Asp Arg Val Gln Phe Gly Pro Val Val Ala Leu Asn Pro Ala Thr
                   500                505                510

Leu Leu Pro Leu Pro Glu Glu Gly Leu Gln His Asn Cys Leu Asp Ile
                   515                520                525

Leu Ala Glu Ala His Gly Thr Arg Pro Asp Leu Thr Asp Gln Pro Leu
    530                535                540

Pro Asp Ala Asp His Thr Trp Tyr Thr Gly Gly Ser Ser Leu Leu Gln
545                550                555                560

Glu Gly Gln Arg Lys Ala Gly Ala Ala Val Thr Thr Glu Thr Glu Val
                   565                570                575

Ile Trp Ala Lys Ala Leu Pro Ala Gly Thr Ser Ala Gln Arg Ala Gln
                   580                585                590

Leu Ile Ala Leu Thr Gln Ala Leu Arg Met Ala Glu Gly Lys Lys Leu
                   595                600                605

Asn Val Tyr Thr Asn Ser Arg Tyr Ala Phe Ala Thr Ala His Ile His
    610                615                620
```

-continued

```
Gly Glu Ile Tyr Arg Arg Arg Gly Leu Leu Thr Ser Glu Gly Lys Glu
625             630             635             640

Ile Lys Asn Lys Asp Glu Ile Leu Ala Leu Leu Lys Ala Leu Phe Leu
            645             650             655

Pro Lys Arg Leu Ser Ile Ile His Cys Pro Gly His Gln Lys Gly His
            660             665             670

Ser Ala Glu Ala Arg Gly Asn Arg Met Ala Asp Gln Ala Ala Arg Lys
        675             680             685

Ala Ala Ile Thr Glu Thr
    690
```